(12) United States Patent
McHardy et al.

(10) Patent No.: US 8,124,639 B2
(45) Date of Patent: Feb. 28, 2012

(54) BICYCLIC [3.1.0] HETEROARYL AMIDES AS TYPE 1 GLYCINE TRANSPORT INHIBITORS

(75) Inventors: Stanton F. McHardy, Conventry, RI (US); John A. Lowe, III, Stonington, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 12/870,928

(22) Filed: Aug. 30, 2010

(65) Prior Publication Data
US 2010/0324020 A1 Dec. 23, 2010

Related U.S. Application Data

(63) Continuation of application No. 11/399,071, filed on Apr. 6, 2006, now abandoned.

(60) Provisional application No. 60/669,472, filed on Apr. 8, 2005.

(51) Int. Cl.
*A61K 31/403* (2006.01)
*A61K 31/4178* (2006.01)
*C07D 403/12* (2006.01)
*C07D 209/52* (2006.01)

(52) U.S. Cl. ............ 514/397; 514/414; 548/314.7; 548/465

(58) Field of Classification Search .......... 514/397, 514/414; 548/333.5, 335.5, 311.1, 465, 314.7
See application file for complete search history.

(56) References Cited

U.S. PATENT DOCUMENTS 7,160,888 B2  1/2007  Johnson et al. .......... 514/253.04

FOREIGN PATENT DOCUMENTS

| JP | 2002212179 | 7/2002 |
| WO | WO9945011 | 9/1999 |
| WO | WO03037865 | 5/2003 |
| WO | WO03089411 | 10/2003 |
| WO | WO2005037216 | 4/2005 |
| WO | WO2005115992 | 12/2005 |

OTHER PUBLICATIONS

Vippagunta et al., Advanced Drug Delivery Reviews, pp. 3-24 (provided in U.S. Appl. No. 11/399,071).*
K. Hashimoto, Recent Patents on CNS Drug Discovery, 2006, vol. 1, p. 43-53.*
Vippagunta, S.R., et al., "Crystalline Solids", Advanced Drug Delivery Reviews, 2001, pp. 3-26, vol. 48.
Wu, et al., "Regulatory perspectives of Type II prodrug development and time-dependent toxicity management: Nonclinical Pharm/Tox analysis and the role of comparative toxicology", Toxicology, 2007, pp. 1-6, vol. 236.
McMurry, John, Chapter 4,Stereochemistry of Alkanes and Cycloalkanes, Organic Chemistry, pp. 100-103, $2^{nd}$ edition, (1988).
Eaton, Philip, et al., "Through-Space Amide Activation of C—H Bonds in Triangulanes", Journal American Chem. Soc., 1993, pp. 11370-11375, vol. 115.
Yoder, Claude, et al., "Matter in Bulk III: Solutions", Chapter 11, Franklin and Marshall College, Chemistry, pp. 252-255, Harcourt Brace Jovanovich, Inc., New York.

* cited by examiner

*Primary Examiner* — Yong Chu
(74) *Attorney, Agent, or Firm* — Gregg C. Benson; Ian Lodovice

(57) ABSTRACT

The present invention relates to a series of substituted bicyclic [3.1.0]heteroaryl amides of the Formula I, wherein A, Q, X, Y, Z and $R_1$-$R_5$ groups are defined as in the specification, that exhibit activity as glycine transport inhibitors, their pharmaceutically acceptable salts, pharmaceutical compositions containing them, and their use for the enhancement of cognition and the treatment of the positive and negative symptoms of schizophrenia and other psychoses in mammals, including humans.

3 Claims, No Drawings

BICYCLIC [3.1.0] HETEROARYL AMIDES AS TYPE 1 GLYCINE TRANSPORT INHIBITORS

CROSS REFERENCE TO RELATED APPLICATION

This application is a continuation of U.S. Ser. No. 11/399,071 filed on Apr. 6, 2006, which claims benefit of U.S. Ser. No. 60/669,472, filed on Apr. 8, 2005, both of which are incorporated by reference in their entirety.

BACKGROUND

The present invention relates to bicyclic[3.1.0]heteroaryl amides and to pharmaceutical compositions containing them and to their use in the treatment of central nervous system disorders, cognitive disorders, schizophrenia, dementia and other disorders in mammals, including humans. These compounds exhibit activity as inhibitors of the glycine type-1 transporter.

Schizophrenia, a progressive neurological disease, is manifested in its early stages as thought disorders such as hallucinations, paranoid delusions, and bizarre thought patterns, collectively known as positive symptoms. These easily recognizable symptoms gave the disease the historical name "madness". As the disease progresses, negative symptoms, such as social withdrawal and anhedonia, and cognitive symptoms such as dementia become more apparent. Only about one-third of schizophrenic patients can be treated successfully and returned to society, while the remainder is generally institutionalized. The burden on society of this devastating illness and the toll it takes on family members of affected patients make it one of the most costly of all CNS diseases.

Pharmacological treatment for schizophrenia has traditionally involved blockade of the dopamine system, which is thought to be responsible for its positive symptoms. Such treatment, however, ignores the negative and cognitive aspects of the disease. Another neurotransmitter system believed to play a role in schizophrenia is the glutamate system, the major excitatory transmitter system in the brain. This hypothesis is based on the observation that blockade of the glutamate system by compounds such as PCP ("angel dust") can replicate many of the symptoms of schizophrenia, including its positive, negative, and cognitive aspects. If schizophrenia involves a deficit of glutamatergic transmission, augmentation of the glutamate system, and specifically the NMDA receptor, may be beneficial. While glutamate is the principle agonist at NMDA receptors, glycine is required as a co-agonist to set the "tone" of the receptor for its response to glutamate. Enhancing this "tone" by increasing the effect of glycine would augment NMDA neurotransmission, and provide potential benefit in the treatment of schizophrenia.

A specific mechanism for augmenting the glycinergic "tone" of the NMDA receptor was disclosed recently by Bergeron, et al. (*Proc. Natl. Acad. Sci. USA*, 95, 15730, (1998)), which is hereby incorporated by reference. This group showed that a specific and potent inhibitor of the glycine type-1 transporter (GlyT1) responsible for removing glycine from the synapse at the NMDA receptor, termed NFPS (WO 97/45115), could enhance NMDA receptor function. For example, NFPS increased the postsynaptic current driven by the NMDA receptor, an effect blocked by both a specific NMDA-site antagonist and a glycine-site antagonist. Even though glycine levels in the brain are high relative to the amount required to act as an NMDA receptor co-agonist, this work shows that GlyT1 removes glycine efficiently at the synapse, and that inhibition of GlyT1 can augment NMDA receptor function. The present invention provides GlyT1 inhibitors as a treatment for disorders or conditions such as schizophrenia through its augmentation of glutamatergic neurotransmission.

SUMMARY OF THE INVENTION

The present invention relates to compounds of Formula I, wherein

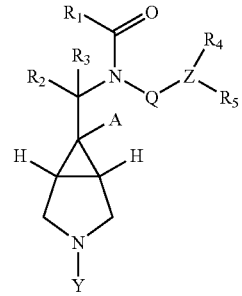

Formula I wherein $R_1$ represents a heteroaryl selected from the group consisting of: imidazolyl, thiazolyl, pyridyl, oxazolyl, pyrazolyl, triazolyl, oxadiazolyl, quinolinyl, isoxazolyl, pyrroloimidazoyl and thiadiazole, wherein said heteroaryl is optionally substituted by one or more substituents selected from —OH, —NR$_7$R$_8$, halogen, ($C_1$-$C_8$)alkyl, ($C_3$-$C_{10}$)cycloalkyl, ($C_1$-$C_8$)alkoxy, ($C_1$-$C_{12}$)alkoxyalkyl, ($C_1$-$C_8$)hydroxyalkyl, ($C_6$-$C_{14}$)aryl and benzyl;

$R_2$, $R_3$ and A independently represent H or ($C_1$-$C_8$)alkyl wherein said alkyl is optionally substituted by one or more —OH, ($C_1$-$C_8$)alkoxy, —NR$_7$R$_8$ or halogen;

Q represents —(CH$_2$)$_n$—, where n=1, 2, 3 or 4 or —(CH$_2$)$_m$—O—, where m=2, 3 or 4;

Z represents ($C_6$-$C_{14}$)aryl, ($C_1$-$C_8$)alkyl or ($C_3$-$C_8$)cycloalkyl;

$R_4$ and $R_5$ each independently represent H, halogen, ($C_1$-$C_8$)alkyl, ($C_6$-$C_{14}$)aryl, ($C_6$-$C_{14}$)aryloxy, ($C_1$-$C_8$)alkoxy, (3-10 membered)heterocycloalkyl or ($C_3$-$C_8$)cycloalkoxy; wherein $R_4$ and $R_5$ are optionally substituted by one or more —OH, ($C_1$-$C_8$)alkoxy, —NR$_7$R$_8$ or halogen;

Y represents —R$_6$, —(CH$_2$)$_o$—R$_6$, —C(R$_6$)$_3$ or —CH(R$_6$)$_2$, wherein o=1, 2 or 3;

$R_6$ represents H, ($C_6$-$C_{14}$)aryl, ($C_1$-$C_{10}$)alkyl, ($C_3$-$C_{10}$)cycloalkyl, ($C_5$-$C_{18}$)bicycloalkyl, ($C_5$-$C_{18}$)tricycloalkyl, (3-10 membered)heterocycloalkyl, (5-10 membered)heteroaryl, —C(=O)NR$_7$R$_8$, or —C(=O)OR$_7$, wherein said R$_6$ groups can optionally be substituted with one or more X groups;

wherein X=—OH, ($C_1$-$C_8$)alkoxy, —NR$_{11}$R$_{12}$, —SO$_2$R$_{10}$, —C(=O)R$_{10}$, halogen, cyano, ($C_1$-$C_8$)alkyl, ($C_1$-$C_{10}$)alkoxyalkyl, (5-10 membered)heteroaryl, ($C_6$-$C_{14}$)aryl, ($C_6$-$C_{14}$)aryloxy, benzyl, or ($C_1$-$C_8$)hydroxyalkyl;

wherein $R_7$ and $R_8$ independently represent H, ($C_1$-$C_8$)alkyl, ($C_3$-$C_8$)cycloalkyl, (5-10 membered)heterocycloalkyl, ($C_1$-$C_8$)hydroxyalkyl, (5-10 membered)heteroaryl or ($C_1$-$C_{10}$)alkoxyalkyl; wherein $R_7$ and $R_8$ may optionally be substituted by one or more X groups;

or $R_7$ and $R_8$ together with the nitrogen in which they may be attached may form a (3-10 membered)heterocycloalkyl group optionally substituted by one or more X groups;

wherein $R_{10}$ represents ($C_1$-$C_8$)alkyl, ($C_3$-$C_8$)cycloalkyl, (3-10 membered)heterocycloalkyl, ($C_1$-$C_8$)hydroxyalkyl, (5-10 membered)heteroaryl or ($C_1$-$C_{10}$)alkoxyalkyl;

wherein $R_{11}$ and $R_{12}$ independently represent H, $(C_1-C_8)$alkyl, $(C_3-C_8)$cycloalkyl, (5-10 membered)heterocycloalkyl, $(C_1-C_8)$hydroxyalkyl, (5-10 membered)heteroaryl or $(C_1-C_{10})$alkoxyalkyl;

or pharmaceutically acceptable salts, solvates or prodrugs thereof.

DETAILED DESCRIPTION OF THE INVENTION

Unless otherwise indicated, as used herein, the terms "halogen" and "halo" include F, Cl, Br, and I.

Unless otherwise indicated, as used herein, the term "alkyl" includes saturated monovalent hydrocarbon radicals having straight or branched moieties. Examples of alkyl groups include, but are not limited to, methyl, ethyl, n-propyl, isopropyl, cyclopropylmethylene (—CH$_2$-cyclopropyl) and t-butyl.

Unless otherwise indicated, as used herein, the term "alkenyl" includes alkyl moieties having at least one carbon-carbon double bond wherein alkyl is as defined above. Examples of alkenyl include, but are not limited to, ethenyl and propenyl.

Unless otherwise indicated, as used herein, the term "alkynyl" includes alkyl moieties having at least one carbon-carbon triple bond wherein alkyl is as defined above. Examples of alkynyl groups include, but are not limited to, ethynyl and 2-propynyl.

Unless otherwise indicated, as used herein, the term "alkoxy", means "alkyl-O—", wherein "alkyl" is as defined above. Examples of "alkoxy" groups include, but are not limited to, methoxy, ethoxy, propoxy, butoxy, pentoxy and allyloxy.

Unless otherwise indicated, as used herein, the term "alkoxyalkyl" means alkyl-O-alkyl-, wherein alkyl is defined above.

Unless otherwise indicated, as used herein, the term "hydroxyalkyl" means -alkyl-OH, wherein alkyl is defined above.

Unless otherwise indicated, as used herein, the term "alkenoxy", means "alkenyl-O—", wherein "alkenyl" is as defined above.

Unless otherwise indicated, as used herein, the term "alkynoxy", means "alkynyl-O—", wherein "alkynyl" is as defined above.

Unless otherwise indicated, as used herein, the term "cycloalkyl" includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl. "Bicycloalkyl" and "tricycloalkyl" groups include non-aromatic saturated cyclic alkyl moieties consisting of two or three rings respectively, wherein said rings share at least one carbon atom. "Bicycloalkyl" and "tricycloalkyl" groups also include cyclic moieties consisting of two or three rings respectively, wherein one ring is aryl or heteroaryl and wherein said rings share two carbon atoms. For purposes of the present invention, and unless otherwise indicated, bicycloalkyl groups include spiro groups and fused ring groups. Examples of bicycloalkyl groups include, but are not limited to, bicyclo-[3.1.0]-hexyl, bicyclo-2.2.1]-hept-1-yl, norbornyl, spiro[4.5] decyl, spiro[4.4]nonyl, spiro[4.3]octyl, spiro[4.2]heptyl, indan, teralene (1,2,3,4-tetrahydronaphlene) and 6,7,8,9-tetrahydro-5H-benzocycloheptene. An example of a tricycloalkyl group is adamantanyl. Other cycloalkyl, bicycloalkyl, and tricycloalkyl groups are known in the art, and such groups are encompassed by the definitions "cycloalkyl", "bicycloalkyl" and "tricycloalkyl" herein. "Cycloalkenyl", "bicycloalkenyl", and "tricycloalkenyl" refer to non-aromatic each cycloalkyl, bicycloalkyl, and tricycloalkyl moieties as defined above, except that they each include one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl, cyclobutenyl, and cyclohexenyl. A non-limiting example of a bicycloalkenyl group is norbornenyl. Cycloalkyl, cycloalkenyl, bicycloalkyl, and bicycloalkenyl groups also include groups that are substituted with one or more oxo moieties. Examples of such groups with oxo moieties are oxocyclopentyl, oxocyclobutyl, oxocyclopentenyl and norcamphoryl. Other cycloalkenyl, bicycloalkenyl, and tricycloalkenyl groups are known in the art, and such groups are included within the definitions "cycloalkenyl", "bicycloalkenyl" and "tricycloalkenyl" herein.

Unless otherwise indicated, as used herein, the term "aryl" includes an organic radical derived from an aromatic hydrocarbon by removal of one hydrogen, such as phenyl (Ph), naphthyl, indenyl, indanyl and fluorenyl. "Aryl" encompasses fused ring groups wherein at least one ring is aromatic.

Unless otherwise indicated, as used herein, the terms "heterocyclic" and "heterocycloalkyl" refer to non-aromatic cyclic groups containing one or more heteroatoms, preferably from one to four heteroatoms, each selected from O, S and N. "Heterobicycloalkyl" groups include non-aromatic two-ringed cyclic groups, wherein said rings share one or two atoms, and wherein at least one of the rings contains a heteroatom (O, S, or N). "Heterobicycloalkyl" groups also include two-ringed cyclic groups, wherein said one ring is aryl or heteroaryl ring and wherein said rings share one or two atoms, and wherein at least one of the rings contains a heteroatom (O, S, or N). Unless otherwise indicated, for purposes of the present invention, heterobicycloalkyl groups include spiro groups and fused ring groups. In one embodiment, each ring in the heterobicycloalkyl contains up to four heteroatoms (i.e. from zero to four heteroatoms, provided that at least one ring contains at least one heteroatom). The heterocyclic groups of this invention can also include ring systems substituted with one or more oxo moieties. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo [3.1.0]hexanyl, 3-azabicyclo[4.1.0]heptanyl, quinolizinyl, quinuclidinyl, 1,4-dioxaspiro[4.5]decyl, 1,4-dioxaspiro[4.4] nonyl, 1,4-dioxaspiro[4.3]octyl, and 1,4-dioxaspiro[4.2]heptyl.

Unless otherwise indicated, as used herein, "heteroaryl" refers to aromatic groups containing one or more heteroatoms, preferably from one to four heteroatoms, selected from O, S and N. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

Unless otherwise indicated, as used herein, the term "cycloalkoxy", means "cycloalkyl-O—", wherein "cycloalkyl" is as defined above.

Unless otherwise indicated, as used herein, the term "aryloxy", means "aryl-O—", wherein "aryl" is as defined above.

Unless otherwise indicated, as used herein, the term "heterocycloalkoxy", means "heterocycloalkyl-O—", wherein "heterocycloalkyl" is as defined above.

Unless otherwise indicated, as used herein, the term "heteroaryloxy", means "heteroaryl-O—", wherein "heteroaryl" is as defined above.

Unless otherwise indicated, all the foregoing groups derived from hydrocarbons may be optionally substituted by one or more halogen atoms (e.g., —$CH_2F$, —$CHF_2$—$CF_3$, -PhCl, etc.).

Unless otherwise indicated, the term "one or more" substituents, or "at least one" substituent as used herein, refers to from one to the maximum number of substituents possible based on the number of available bonding sites. (Examples of one or more or at least one substituent include, but are not limited to, 1 to 10 substituents, or 1 to 6 substituents or 1 to 3 substituents).

Unless otherwise indicated, all the foregoing groups derived from hydrocarbons may have up to about 1 to about 20 carbon atoms (e.g. $C_1$-$C_{20}$ alkyl, $C_2$-$C_{20}$ alkenyl, $C_3$-$C_{20}$ cycloalkyl, (3-20 membered)heterocycloalkyl, $C_6$-$C_{20}$ aryl, (5-20 membered)heteroaryl, etc.) or 1 to about 15 carbon atoms (e.g., $C_1$-$C_{15}$ alkyl, $C_2$-$C_{15}$ alkenyl, $C_3$-$C_{15}$ cycloalkyl, (3-15 membered)heterocycloalkyl, $C_6$-$C_{15}$ aryl, (5-15 membered)heteroaryl, etc.), or 1 to about 12 carbon atoms, or 1 to about 8 carbon atoms, or 1 to about 6 carbon atoms.

The foregoing groups, as derived from the compounds listed above, may be C-attached or N-attached where such is possible. For instance, a group derived from pyrrole may be pyrrol-1-yl (N-attached) or pyrrol-3-yl (C-attached). The terms referring to the groups also encompass all possible tautomers.

In one aspect of the invention, the stereochemistry is defined as in Formula II or Formula III:

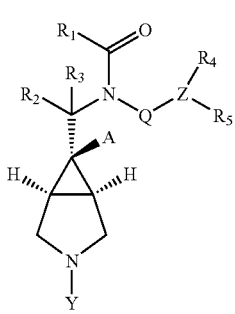

Formula II

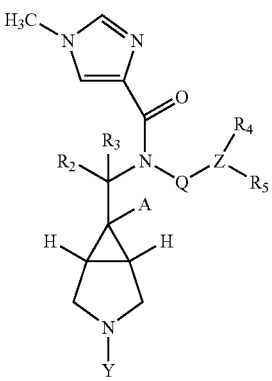

Formula III

In one aspect of this invention, $R_1$ is imidazolyl optionally substituted by methyl.

In another aspect, Z is ($C_6$-$C_{14}$)aryl, and $R_4$ or $R_5$ are each independently H, halogen, —$CF_3$, —$OCF_3$, ($C_6$-$C_{14}$)aryl or ($C_6$-$C_{14}$)aryloxy.

In yet another aspect of the invention, $R_2$, $R_3$ and A are hydrogen.

In another aspect, Y is a ($C_1$-$C_6$)alkyl, a ($C_3$-$C_6$)cycloalkyl, a (3-6 membered)heterocycloalkyl or —$CH_2$—($C_3$-$C_6$)cycloalkyl; wherein Y is optionally substituted by halogen, OH, —$SO_2R_{10}$, —C(=O)$R_{10}$, or $CH_2CH_2CF_3$.

In another aspect of this invention, the compound of Formula I has the following structure:

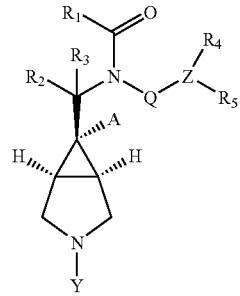

wherein $R^2$-$R^5$, Q, Z, Y and A are as defined above.

Specific embodiments of the present invention are shown in the Examples below.

Compounds of the Formula I may have optical centers and therefore may occur in different enantiomeric and diastereomeric configurations. The present invention includes all enantiomers, diastereomers, and other stereoisomers of such compounds of the Formula I, as well as racemic compounds and racemic mixtures and other mixtures of stereoisomers thereof.

Pharmaceutically acceptable salts of the compounds of Formula I include the acid addition and base salts thereof.

Suitable acid addition salts are formed from acids which form non-toxic salts. Examples include, but are not limited to, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mandelates mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, salicylate, saccharate, stearate, succinate, sulfonate, stannate, tartrate, tosylate, trifluoroacetate and xinofoate salts.

Suitable base salts are formed from bases which form non-toxic salts. Examples include, but are not limited to, the aluminum, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002).

Pharmaceutically acceptable salts of compounds of Formula I may be prepared by one or more of three methods:

(i) by reacting the compound of Formula I with the desired acid or base;

(ii) by removing an acid- or base-labile protecting group from a suitable precursor of the compound of Formula I or by ring-opening a suitable cyclic precursor, for example, a lactone or lactam, using the desired acid or base; or (iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —$COO^-Na^+$, —$COO^-K^+$, or —$SO_3^-Na^+$) or non-ionic (such as —$N^-N^+(CH_3)_3$) polar head group. For more information, see Crystals and the Polarizing Microscope by N. H. Hartshorne and A. Stuart, $4^{th}$ Edition (Edward Arnold, 1970).

Hereinafter all references to compounds of Formula I include references to salts, solvates, multi-component complexes and liquid crystals thereof and to solvates, multi-component complexes and liquid crystals of salts thereof.

The compounds of the invention include compounds of Formula I as hereinbefore defined, including all polymorphs and crystal habits thereof, prodrugs and isomers thereof (including optical, geometric and tautomeric isomers) as hereinafter defined and isotopically-labeled compounds of Formula I.

As indicated, so-called 'prodrugs' of the compounds of Formula I are also within the scope of the invention. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985).

Some examples of prodrugs in accordance with the invention include, but are not limited to, (i) where the compound of Formula I contains a carboxylic acid functionality (—COOH), an ester thereof, for example, a compound wherein the hydrogen of the carboxylic acid functionality of the compound of Formula (I) is replaced by $(C_1-C_8)$alkyl;

(ii) where the compound of Formula I contains an alcohol functionality (—OH), an ether thereof, for example, a compound wherein the hydrogen of the alcohol functionality of the compound of Formula I is replaced by $(C_1-C_6)$alkanoyloxymethyl; and (iii) where the compound of Formula I contains a primary or secondary amino functionality (—$NH_2$ or —NHR where R≠H), an amide thereof, for example, a compound wherein, as the case may be, one or both hydrogens of the amino functionality of the compound of Formula I is/are replaced by $(C_1-C_{10})$alkanoyl.

Further examples of replacement groups in accordance with the foregoing examples and examples of other prodrug types may be found in the aforementioned references.

Moreover, certain compounds of Formula I may themselves act as prodrugs of other compounds of Formula I.

Also included within the scope of the invention are metabolites of compounds of Formula I, that is, compounds formed in vivo upon administration of the drug. Some examples of metabolites in accordance with the invention include, but are not limited to, (i) where the compound of Formula I contains a methyl group, an hydroxymethyl derivative thereof (—$CH_3$→—$CH_2OH$):

(ii) where the compound of Formula I contains an alkoxy group, an hydroxy derivative thereof (—OR→OH);

(iii) where the compound of Formula I contains a tertiary amino group, a secondary amino derivative thereof (—$NR^1R^2$→—$NHR^1$ or —$NHR^2$);

(iv) where the compound of Formula I contains a secondary amino group, a primary derivative thereof (—$NHR^1$→$NH_2$);

(v) where the compound of Formula I contains a phenyl moiety, a phenol derivative thereof (-Ph→-PhOH); and (vi) where the compound of Formula I contains an amide group, a carboxylic acid derivative thereof (—$CONH_2$→COOH).

Compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate or racemic mixture (or a racemic precursor) may be reacted with a suitable optically active compound, for example, an alcohol, or, in the case where the compound of Formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

The present invention includes all pharmaceutically acceptable isotopically-labelled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formula I, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

When preparing compounds of Formula I in accordance with the invention, it is open to a person skilled in the art to routinely select the form of compound of Formula II which provides the best combination of features for this purpose. Such features include, but are not limited to, the melting point, solubility, processability and yield of the intermediate form and the resulting ease with which the product may be purified on isolation.

This invention also relates to a method of treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia, and senile dementia of the Alzheimer's type) and memory disorders in a mammal, including a human, comprising administering to a mammal in need of such treatment an amount of a compound of the formula I, or a pharmaceutically acceptable salt thereof, that is effective in treating such condition or disorder.

This invention also relates to a pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia and senile dementia of the Alzheimer's type) and memory disorders in a mammal, including a human, comprising a compound of the formula I, or a pharmaceutically acceptable salt thereof, in an amount that is effective for treating such disorder or condition.

This invention also relates to a method of treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia and senile dementia of the Alzheimer's type) and memory disorders in a mammal, including a human, comprising administering to a mammal in need of such treatment a glycine transport-inhibiting amount of a compound of the formula I, or a pharmaceutically acceptable salt thereof.

This invention also relates to a pharmaceutical composition for treating a disorder or condition selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; movement disorders such as Tourette's syndrome, akinetic-rigid syndrome, movement disorders associated with Parkinson's disease, tardive dyskinesia and other drug induced and neurodegeneration based dyskinesias; attention deficit hyperactivity disorder; cognitive disorders such as dementias (including age related dementia and senile dementia of the Alzheimer's type) and memory disorders in a mammal, including a human, comprising a compound of the formula I, or a pharmaceutically acceptable salt thereof, in a glycine transport-inhibiting amount.

As used herein, the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

The compounds of the present invention exhibit glycine transport inhibiting activity and therefore are of value in the treatment of a wide variety of clinical conditions that are characterized by the deficit of glutamateric neurotransmission in mammalian subjects, especially humans. Such conditions include the positive and negative symptoms of schizophrenia and other psychoses, and cognitive deficits.

The compounds of this invention can be administered via either the oral, parenteral (such as subcutaneous, intravenous, intramuscular, intrasternal and infusion techniques), rectal, intranasal or topical routes to mammals. In general, these compounds are most desirably administered to humans in doses ranging from about 1 mg to about 2000 mg per day, although variations will necessarily occur depending upon the weight and condition of the subject being treated and the particular route of administration chosen. However, a dosage level that is in the range of from about 0.1 mg to about 20 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

In one embodiment, the compounds of this invention are administered as adjunctive therapy with known anti-psychotics such as Ziprasidone (Geodon), Clozapine, Molindone, Loxapine, Pimozide, Risperidone, Olanzapine, Remoxipride, Sertindole, Amisulpride, Quetiapine, Prochlorperazine, Fluphenazine, Trifluoroperazine, Thioridazine, Haloperidol, Chloropromazine, Flupentixol and Pipotiazine.

In another embodiment, the compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), anti-Alzheimer's drugs such as donepezil, tacrine, $\alpha 2\delta$ inhibitors, COX-2 inhibitors, gaba pentenoids, propentofylline or metryfonate, and antipyschotics such as PDE10 inhibitors, 5HT2C agonists, alpha 7 nicotinic receptor agonists, CB1 antagonists and compounds having activity antagonizing dopamine D2 receptors.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of the present invention were assayed utilizing the GlyT1 radioligand binding assay described below:

Test compound preparation: Compounds are dissolved in DMSO, sonicated if necessary, diluted to a concentration of 0.2 mM in DMSO and then diluted with de-ionized water to a concentration of 10 uM.

Tissue preparation: The GlyT1c transporter is expressed in HEK-293 cells and the frozen cell pellet weighed and polytroned, with 1 gram cell pellet in 30 mL assay buffer (50 mM Tris base, 120 mM NaCl, and 5 mM KCl, pH'd to 7.4 with 6N HCl). The mixture is centrifuged at 40000 G for 10 min., the supernatant decanted, and the pellet resuspended at 1 mg wet weight per 25 uL assay buffer.

Assay: The assay incubation is carried out for 60 min. at room temperature in 96 well plates (Beckman 2 mL polypropylene), which are vortexed upon addition of the tissue preparation. To each well is added 25 uL test drug solution or control, 200 uL of 0.7 nM [3H]-NPTS (Lowe, John A.; Drozda, Susan E.; Fisher, Katherine; Strick, Christine; Lebel, Lorraine; Schmidt, Christopher; Hiller, Donna; Zandi, Kathleen S. [3H]-(R)-NPTS, a radioligand for the type 1 glycine transporter. Bioorganic & Medicinal Chemistry Letters (2003), 13(7), 1291-1292.), and 25 uL tissue. The plates are filtered using a Brandel cell harvester with GF/B filters, the filters are washed with 3×1.5 mL assay buffer, air-dried overnight, and counted on a LKB beta plate counter the next day.

Compounds of the invention analyzed by this assay have been found to have significant activity in inhibiting glycine reuptake in synaptosomes, having greater than 20% inhibition at 1 µM.

The compounds of the Formula I may be prepared by the methods described below, together with synthetic methods known in the art of organic chemistry, or modifications and derivatisations that are familiar to those of ordinary skill in the art. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, *Protective Groups in Organic Chemistry*, John Wiley & Sons, 1981; and T. W. Greene and P. G. M. Wuts, *Protective Groups in Organic Chemistry*, John Wiley & Sons, 1991, which are hereby incorporated by reference.

Compounds of formula I or their pharmaceutically acceptable salts, can be prepared according to the following reaction Schemes I through V as discussed herein below. Unless otherwise indicated A, Q, Y, Z and $R_1$ through $R_5$ are defined as above. Isolation and purification of the products is accomplished by standard procedures, which are known to a chemist of ordinary skill.

The following schemes are exemplary of the processes for making compounds of formula I.

Scheme I illustrates a method for the preparation of compounds having the basic structure of formula I, where A is hydrogen, Y is hydrogen and Q, Z and $R_1$ through $R_8$ are defined as above.

Referring to Scheme I, a compound of formula (I) [*SynLett*, 1996, 1097] can be treated with $(BOC)_2O$ in the presence of a suitable base such as triethylamine, in solvents such as $CH_2Cl_2$, to produce the desired carbamate of formula (II). Oxidation of the primary alcohol under Swern conditions with DMSO and oxayl chloride, in the presence of a suitable base such as triethyl amine (TEA) or diisopropylethylamine (DIEA), in solvents such as $CH_2Cl_2$ or 1,2-dichloroethane (DCE), at temperatures ranging from −78° C. to room temperature, preferably at about room temperature, to produce the corresponding aldehyde (not depicted). Other suitable oxidation reagents for this transformation include TPAP/NMO or PCC.

Treatment of the aldehyde with an appropriately substituted amine reagent of formula (III) and a suitable reducing agent such as $NaBH_4$, in a solvent such as MeOH, at temperatures ranging from −5° C. to room temperature, preferably at about room temperature, produced the desired amine of formula (IV). Other suitable reducing agents for this reaction include $NaCNBH_3$ or $NaHB(OAc)_3$, in solvents such as MeOH, $CH_2Cl_2$ or DCE. Other suitable conditions for this transformation include treatment of the corresponding aldehyde with the amine reagent (III) in $CH_2Cl_2$ or DCE in the presence of 4 Å molecular sieves and a base such as TEA at room temperature, followed by treatment with $NaBH_4$ or $NaHB(OAc)_3$.

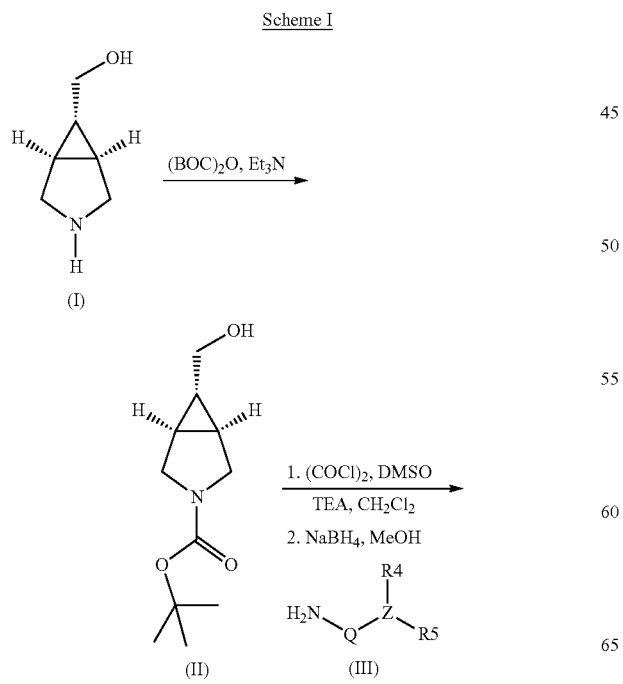

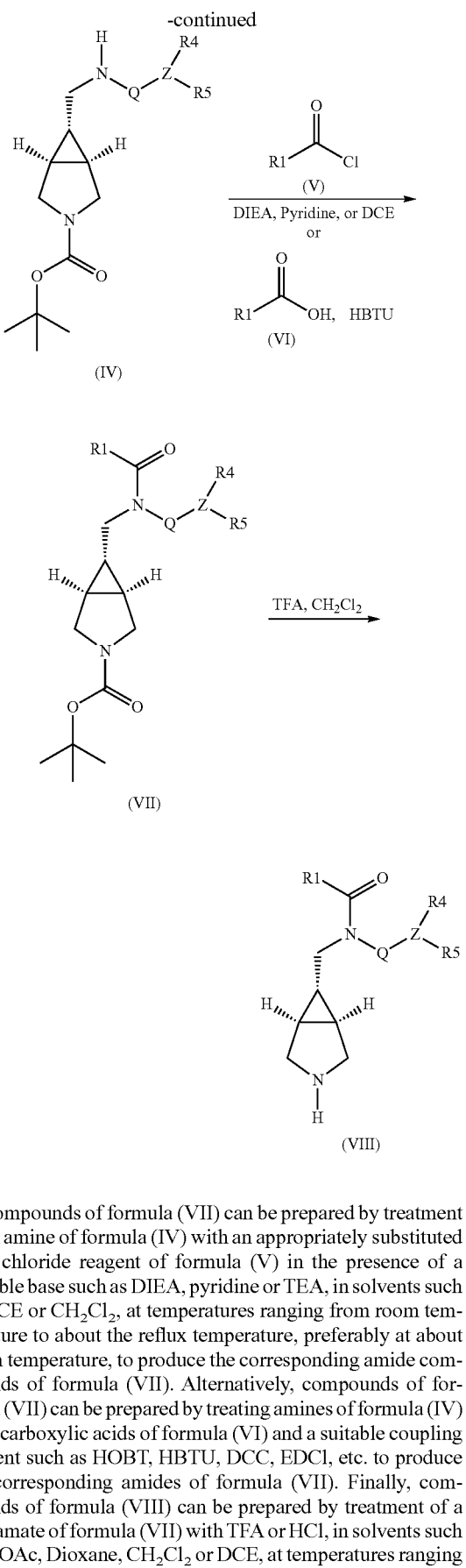

Compounds of formula (VII) can be prepared by treatment of an amine of formula (IV) with an appropriately substituted acid chloride reagent of formula (V) in the presence of a suitable base such as DIEA, pyridine or TEA, in solvents such as DCE or $CH_2Cl_2$, at temperatures ranging from room temperature to about the reflux temperature, preferably at about room temperature, to produce the corresponding amide compounds of formula (VII). Alternatively, compounds of formula (VII) can be prepared by treating amines of formula (IV) with carboxylic acids of formula (VI) and a suitable coupling reagent such as HOBT, HBTU, DCC, EDCl, etc. to produce the corresponding amides of formula (VII). Finally, compounds of formula (VIII) can be prepared by treatment of a carbamate of formula (VII) with TFA or HCl, in solvents such as EtOAc, Dioxane, $CH_2Cl_2$ or DCE, at temperatures ranging from 0° C. to about room temperature, preferably at about room temperature, to produce the corresponding amine of formula (VIII).

Scheme II illustrates a method for the preparation of compounds having the basic structure of formula I, where A is hydrogen and Y, Q, Z and R$_1$-R$_6$ are described as above.

Referring to scheme II below, compounds of formula (IX) can be prepared by treatment of an amine of formula (VIII) with an appropriately substituted aldehyde or ketone and a reducing agent such as NaHB(OAc)$_3$, in solvents such as CH$_2$Cl$_2$ or DCE, at temperatures ranging from 0° C. to about room temperature, preferably at about room temperature, to produce the corresponding amine of formula (IX). Other suitable conditions for this process include treatment of the amine of formula (VIII) with an aldehyde in toluene, at about the reflux temperature; followed by treatment with NaBH$_4$, in solvents such as MeOH, produce the corresponding amine of formula (IX). Also, treatment of an amine of formula (VIII) with an aldehyde and NaCNBH$_3$ in a solvent such as MeOH, produce the corresponding amine of formula (IX).

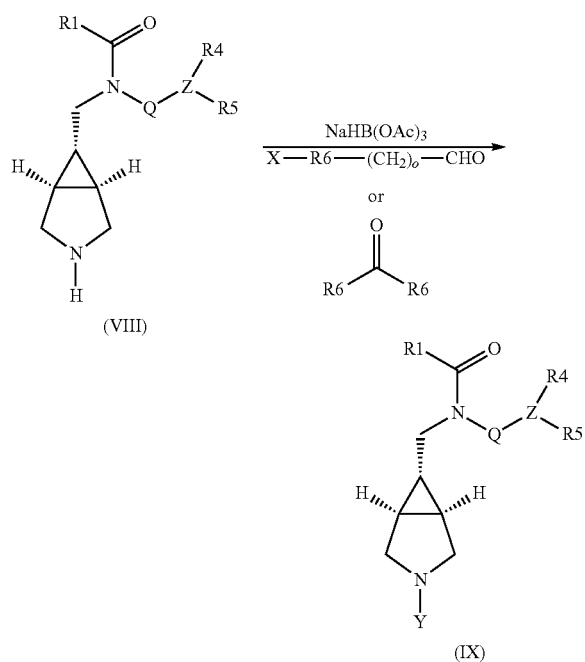

Scheme III illustrates an alternative method for the preparation of compounds having the basic structure of formula I, where A is hydrogen and Y, Q, Z and R$_1$-R$_5$ are described as above. R$_9$ is a cycloalkyl, —(CH$_2$)$_o$—R$_6$, —CH(R$_6$) or —C(R$_6$)$_2$.

Referring to scheme III below, a compound of formula (VIII) can be treated with an epoxide reagent of formula (X) in the presence of a suitable base such as triethyl amine, in solvents such as methanol or ethanol, at temperatures ranging from room temperature to about the reflux temperature, preferably at about the reflux temperature, to produce compounds of formula (IX).

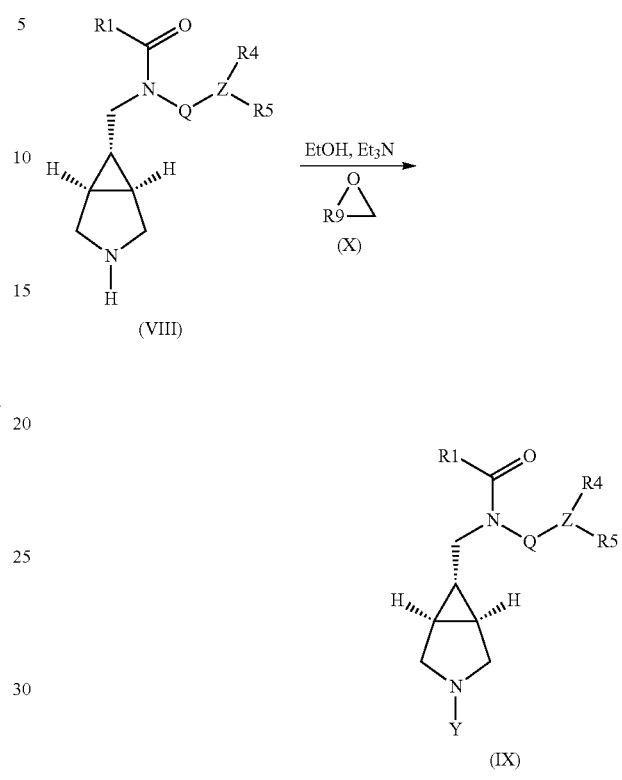

Scheme IV below illustrates an alternative method for the preparation of compounds having the basic structure of formula I, where A is hydrogen and Y, Q, Z and R$_1$-R$_5$ are described as above.

Referring to scheme IV below, compounds of formula (XIII) can be treated with a suitable base such as NaH or KH, and an appropriately substituted alkylating agent of formula (XI), where L is a suitable leaving group such as Cl, Br, I, OMs, OTs, in solvents such as THF or ether, at temperatures ranging from 0° C. to about room temperature, preferably at about room temperature, to produce the compounds of formula (IX).

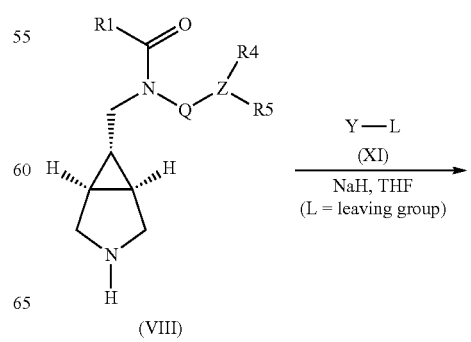

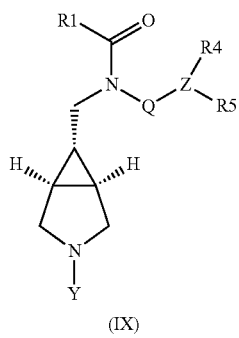

(IX)

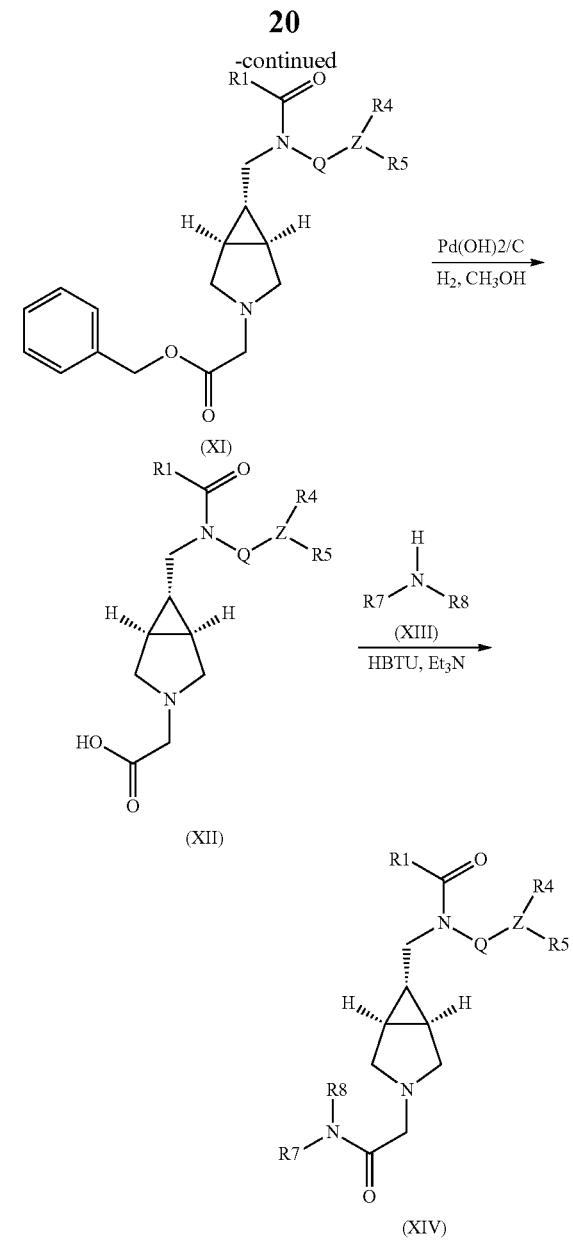

Scheme V below illustrates an alternative method for the preparation of compounds having the basic structure of formula I, where A is hydrogen and Y, Q, Z and $R_1$-$R_8$ are described as above.

Referring to scheme V below, compounds of formula (VIII) can be treated with a suitably protected alpha-bromo ester derivative of formula (X), such as alpha-bromo benzyl acetate, in the presence of a base such as potassium carbonate, a suitable ammonium salt such as tetraethyl ammonium chloride and a suitable solvent such as dimethyl formamide, at room temperature to yield the desired compound of formula (XI). Compound of formula (XI) can be treated with a suitable palladium catalyst, such as palladium hydroxide, in solvents such as methanol or ethanol, to produce compounds of formula (XII). Finally, compounds of formula (XIV) can be prepared by treating the acid of formula (XII) with primary and secondary amines of general formula (XIII) in the presence of suitable coupling agents such as O-Benzotriazol-1-yl-N,N,N',N'-tetramethyluronium hexafluorophosphate (HBTU) and triethyl amine, to produce the desired compounds of formula (XIV).

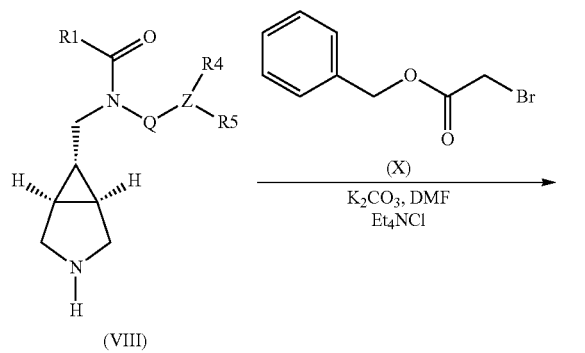

The following examples and preparations illustrate the present invention. It is to be understood, however, that the invention, as fully described herein and as recited in the claims, is not intended to be limited by the details of the following examples.

Examples

Preparation 1

6-Hydroxymethyl-3-aza-bicyclo[3.1.0]hexane-3-carboxylic acid tert-butyl ester

To a solution of (3-Aza-bicyclo[3.1.0]hex-6-yl)-methanol-HCl (11.8 gm, 78.7 mmol) in 350 mL of anhydrous $CH_2Cl_2$ at room temperature was added $Et_3N$ (32.9 mL, 236 mmol), followed by $(BOC)_2O$ (18.9 gm, 86.6 mmol) in portions. The reaction was stirred at room temperature for 18 hours. The mixture was washed with saturated $NaHCO_3$, water, brine and dried over anhydrous $MgSO_4$. The mixture was filtered and concentrated under reduced pressure to yield the crude material, which was purified via flash chromatography with 10% MeOH/CH$_2$Cl$_2$. The product containing fractions were collected and concentrated to yield 6-Hydroxymethyl-3-aza-bicyclo[3.1.0]hexane-3-carboxylic acid tert-butyl ester (15.6 gm). 400 MHz $^1$H NMR (CDCl$_3$) δ 3.4-3.6 (m, 4H), 3.2-3.7 (m, 2H), 1.72 (brs, 1H), 1.4-1.4 (m, 10H), 0.9-0.9 (m, 1H); MS (M+1) 213.2.

Preparation 2

6-Formyl-3-aza-bicyclo[3.1.0]hexane-3-carboxylic acid tert-butyl ester

To a stirring solution of oxalyl chloride (7.8 mL, 89.5 mmol) in 370 mL of anhydrous CH$_2$Cl$_2$ at −78° C., under Nitrogen, was added DMSO (13.8 mL, 193.9 mmol) dropwise. After 10 minutes, 6-Hydroxymethyl-3-aza-bicyclo[3.1.0]hexane-3-carboxylic acid tert-butyl ester (15.9 gm, 74.5 mmol) in 72 mL anhydrous CH$_2$Cl$_2$ was added. After the mixture stirred 30 minutes, triethylamine (52.0 mL, 372.9 mmol) was added and the mixture was allowed to slowly warm to 0° C. over 1 hour. The mixture was concentrated, the resulting solid was taken up in saturated NaHCO$_3$ and EtOAc, the layers were separated and the aqueous layer was extracted with EtOAc. The combined organic layers were washed with brine, dried, filtered and concentrated to give a quantitative crude yield of 6-Formyl-3-aza-bicyclo[3.1.0]hexane-3-carboxylic acid tert-butyl ester (15.8 gm), which was used in the next step without purification. 400 MHz $^1$H NMR (CDCl$_3$) δ 9.4 (d, J=4.1 Hz, 1H), 3.6 (dd, J=11.2 Hz, 37.8 Hz, 2H), 3.4 (d, J=9.95, 2H), 2.1 (m, 2H), 1.8-1.7 (q, J=3.32 Hz, 1H), 1.4 (s, 9H); GCMS (M+0) 211.0.

Preparation 3

6-[(3-Trifluoromethoxy-benzylamino)-methyl]-3-aza-bicyclo[3.1.0]hexane-3-carboxylic acid tert-butyl ester To a stirring solution of the aldehyde prepared above (1.0 g, 4.7 mmol) in 9.5 mL of MeOH was added 3-trifluoromethoxy-benzylamine (0.7 mL, 4.7 mmol). The reaction mixture was stirred at room temperature for 24 hours. Sodium borohydride (0.4 g, 9.5 mmol) was then added and the reaction mixture stirred for another 24 hours. The reaction was concentrated under reduced pressure and the resulting material was taken up in 1 N NaOH and extracted with CH$_2$Cl$_2$. The combined organic layers were dried over anhydrous MgSO$_4$, filtered and concentrated under reduced pressure to yield 1.8 gm of the desired amine, which was taken on without purification. 6-[(3-Trifluoromethoxy-benzylamino)-methyl]-3-azabicyclo[3.1.0]hexane-3-carboxylic acid tert-butyl ester 400 MHz $^1$H NMR (CDCl$_3$) δ 7.3 (t, J=7.8 Hz, 1H), 7.2 (m, 1H), 7.2 (s, 1H), 7.1-7.0 (m, 1H), 3.8 (s, 2H), 3.5 (dd, J=39.4 Hz, 10.8 Hz, 2H), 3.8 (t, J=10.8 Hz, 2H), 2.5 (dt, J=6.0 Hz, 25.7 Hz, 2H), 1.4 (s, 9H), 1.3 (m, 2H) 0.8-0.7 (m, 1H); MS (M+1) 387.3.

The following compounds were made using the procedure described in preparation 3.

6-[(3-Trifluoromethyl-benzylamino)-methyl]-3-aza-bicyclo[3.1.0]hexane-3-carboxylic acid tert-butyl ester 400 MHz $^1$H NMR (CDCl$_3$) δ 7.5 (s, 1H), 7.5-7.2 (m, 3H), 3.8 (s, 2H), 3.5 (dd, J=37.7 Hz, 10.8 Hz, 2H), 3.2 (m, 2H), 2.5 (dt, J=17.0 Hz, 5.4 Hz, 2H), 1.4 (s, 9H), 1.3-1.2 (m, 2H) 0.8-0.7 (m, 1H); MS (M+1) 371.3.

6-[(3-Chloro-benzylamino)-methyl]-3-aza-bicyclo[3.1.0]hexane-3-carboxylic acid tert-butyl ester 400 MHz $^1$H NMR (CDCl$_3$) δ 7.3 (s, 1H), 7.2-7.1 (m, 3H), 3.8 (s, 2H), 3.5 (dd, J=37.3 Hz, 10.8 Hz, 2H), 3.3-3.3 (m, 2H), 2.6-2.5 (m, 2H), 1.4 (m, 9H), 1.3 (m, 2H) 0.8-0.7 (m, 1H); MS (M+1) 337.2.

6-[(4-Fluoro-3-trifluoromethyl-benzylamino)-methyl]-3-aza-bicyclo[3.1.0]hexane-3-carboxylic acid tert-butyl ester 400 MHz $^1$H NMR (CDCl$_3$) δ 7.6-7.5 (m, 1H), 7.5-7.4 (m, 1H), 7.2 (s, 1H), 3.8 (s, 1H) 3.6-3.5 (m, 4H), 2.5-2.5 (m, 2H), 1.4 (s, 9H), 1.3-1.2 (m, 2H) 0.8-0.7 (m, 1H); MS (M+1) 389.3.

6-[(3-Chloro-4-fluoro-benzylamino)-methyl]-3-aza-bicyclo[3.1.0]hexane-3-carboxylic acid tert-butyl ester 400 MHz $^1$H NMR (CDCl$_3$) δ 7.3-7.4 (m, 1H); 7.0-7.2 (m, 2H); 3.7 (3, 2H); 3.4-3.6 (m, 2H); 3.3-3.4 (m, 2H); 2.4-2.6 (m, 2H); 1.4 (m, 9H); 1.3 (m, 2H); 0.8 (m, 1H).

Preparation 4

6-{[(1-Methyl-1H-imidazole-4-carbonyl)-(3-trifluoromethoxy-benzyl)-amino]-methyl}-3-aza-bicyclo[3.1.0]hexane-3-carboxylic acid tert-butyl ester To a stirring solution of 6-[(3-Trifluoromethoxy-benzylamino)-methyl]-3-aza-bicyclo[3.1.0]hexane-3-carboxylic acid tert-butyl ester prepared above (5.9 gm, 15.4 mmol) in 192 mL of CH$_3$CN at room temperature under N$_2$ was added DIEA (8.0 mL, 46.1 mmol) and 1-Methyl-1H-imidazole-4-carbonyl chloride HCL (5.6 gm, 30.7 mmol). After 24 hours, reaction was quenched with H$_2$O, extracted with EtOAc. Organic layer was then washed with a 10% Citric acid solution, H$_2$O, NaHCO$_3$, and brine. The combined extracts were dried over anhydrous MgSO$_4$, filtered and concentrated under reduced pressure, to yield 6.7 gm of 6-{[(1-Methyl-1H-imidazole-4-carbonyl)-(3-trifluoromethoxy-benzyl)-amino]-methyl}-3-aza-bicyclo[3.1.0]hexane-3-carboxylic acid tert-butyl ester 400 MHz $^1$H NMR (CDCl$_3$) δ 7.8 (d, J=1.2 Hz, 1H), 7.3-7.1 (m, 5H), 5.4 (s, 1H), 4.8-4.7 (m, 1H), 4.2 (m, 1H), 3.7 (s, 1H), 3.7 (s, 3H), 3.4-3.2 (m, 3H), 1.4 (s, 9H), 1.3 (m, 2H), 0.8 (m, 1H); MS (M+1) 495.3.

The following compounds were made using the procedure described in preparation 4.

6-{[(1-Methyl-1H-imidazole-4-carbonyl)-(3-trifluoromethyl-benzyl)-amino]-methyl}-3-aza-bicyclo[3.1.0]hexane-3-carboxylic acid tert-butyl ester 400 MHz $^1$H NMR (CDCl$_3$) δ 7.6-7.2 (m, 6H), 5.4 (s, 1H), 4.9-4.8 (m, 1H), 4.2 (m, 1H), 3.7 (s, 3H), 3.4-3.2 (m, 7H), 1.4 (m, 9H), 0.8 (m, 1H); LCMS (M+0) 479.1.

6-{[(3-Chloro-benzyl)-(1-methyl-1H-imidazole-4-carbonyl)-amino]-methyl}-3-aza-bicyclo[3.1.0]hexane-3-carboxylic acid tert-butyl ester 400 MHz $^1$H NMR (CDCl$_3$) δ 7.6 (s, 1H), 7.4 (s, 1H), 7.2-7.1 (m, 4H), 5.4 (d, 1H), 4.8-4.7 (m, 1H), 4.2 (m, 1H), 3.8

(s, 1H), 3.7 (s, 3H), 3.5-3.4 (m, 2H), 3.3-3.2 (m, 2H), 1.4 (s, 9H), 1.4-1.3 (m, 2H), 0.8 (m, 1H); MS (M+1) 445.3.

6-{[(4-Fluoro-3-trifluoromethyl-benzyl)-(1-methyl-1H-imidazole-4-carbonyl)-amino]-methyl}-3-aza-bicyclo[3.1.0]hexane-3-carboxylic acid tert-butyl ester 400 MHz $^1$H NMR (CDCl$_3$) δ 7.6 (s, 1H), 7.5 (m, 2H), 7.3 (m, 1H), 7.1 (t, J=9.5 Hz, 1H), 5.4 (s, 1H), 4.8-4.7 (m, 1H), 4.2 (m, 1H), 3.9-3.8 (m, 1H), 3.7 (s, 3H), 3.5 (m, 1H), 3.4-3.2 (m, 4H), 1.4 (m, 2H), 1.4 (s, 9H), 0.8 (m, 1H); MS (M+1) 497.3.

6-{[(3-Chloro-4-fluoro-benzyl)-(1-methyl-1H-imidazole-4-carbonyl)-amino]-methyl}-3-aza-bicyclo[3.1.0]hexane-3-carboxylic acid tert-butyl ester 400 MHz $^1$H NMR (CDCl$_3$) δ 7.6 (s, 1H); 7.3-7.4 (m, 2H); 7.1-7.2 (m, 1H); 7.0-7.1 (t, J=8.7 Hz, 1H); 5.3-5.4 (m, 1H); 4.6-4.8 (m, 1H); 4.1-4.2 (m, 1H); 3.7 (m, 3H); 3.2-3.5 (m, 5H); 1.3-1.4 (m, 11H); 0.8 (m, 1H); MS (M+1) 463.0.

Example 1

1-Methyl-1H-imidazole-4-carboxylic acid (3-aza-bicyclo[3.1.0]hex-6-ylmethyl)-(3-trifluoromethoxy-benzyl)-amide Hydrochloride To 6-{[(1-Methyl-1H-imidazole-4-carbonyl)-(3-trifluoromethoxy-benzyl)-amino]-methyl}-3-aza-bicyclo[3.1.0]hexane-3-carboxylic acid tert-butyl ester prepared above (7.74 gm, 15.65 mmol) was added 5 mL of saturated HCl in EtOAc at room temperature. The reaction stirred at room temperature for 4 hours. The mixture was concentrated under reduced pressure to yield 6.63 gm of 1-Methyl-1H-imidazole-4-carboxylic acid (3-aza-bicyclo[3.1.0]hex-6-ylmethyl)-(3-trifluoromethoxy-benzyl)-amide Hydrochloride.

400 MHz $^1$H NMR (CD$_3$OD) δ 9.0 (s, 1H), 8.2 (brs, 1H), 7.5-7.2 (m, 4H), 5.0, brs, 2H), 4.0-3.9 (m, 4H), 3.6-3.4 (m, 2H), 3.3 (m, 3H), 1.8 (brs, 2H), 1.32 (brs, 1H); MS (M+1) 395.3.

The following compounds were made using the procedure described in example 1.

Example 2

1-Methyl-1H-imidazole-4-carboxylic acid (3-aza-bicyclo[3.1.0]hex-6-ylmethyl)-(3-trifluoromethyl-benzyl)-amide Hydrochloride 400 MHz $^1$H NMR (CD$_3$OD) δ 9.0 (s, 1H), 8.2 (brs, 1H), 7.6 (m, 4H), 5.0 (brs, 2H), 4.0-3.9 (m, 4H), 3.6 (m, 2H), 3.3-3.2 (m, 3H), 1.8 (brs, 2H), 1.2 (brs, 1H).

Example 3

1-Methyl-1H-imidazole-4-carboxylic acid (3-aza-bicyclo[3.1.0]hex-6-ylmethyl)-(3-chloro-benzyl)-amide Hydrochloride 400 MHz $^1$H NMR (CD$_3$OD) δ 9.0 (s, 1H), 8.2 (brs, 1H), 7.3-7.2 (m, 4H), 5.0, brs, 2H), 4.-3.9 (m, 4H), 3.56 (m, 2H), 3.3 (m, 3H), 1.8 (brs, 2H), 1.2 (brs, 1H); MS (M+1) 345.1.

Example 4

1-Methyl-1H-imidazole-4-carboxylic acid (3-aza-bicyclo[3.1.0]hex-6-ylmethyl)-(4-fluoro-3-trifluoromethyl-benzyl)-amide Hydrochloride 400 MHz $^1$H NMR (CD$_3$OD) δ 9.0 (s, 1H), 8.2 (brs, 1H), 7.6 (m, 2H), 7.4 (s, 1H), 4.9 (brs, 2H), 4.0 (m, 4H), 3.6-3.4 (m, 2H), 3.3 (s, 3H), 1.8 (brs, 2H), 1.4 (brs, 1H).

Example 5

1-Methyl-1H-imidazole-4-carboxylic acid (3-aza-bicyclo[3.1.0]hex-6-ylmethyl)-(3-chloro-4-fluoro-benzyl)-amide Hydrochloride 400 MHz 1HNMR (CD$_3$OD) δ 9.1 (s, 1H); 8.3 (brs, 1H); 7.5 (m, 1H); 7.2-7.4 (m, 2H); 4.8-5.2 (m, 4H); 3.9-4.1 (m, 3H); 3.5-3.6 (m, 2H); 3.2-3.3 (m, 2H); 1.8 (m, 3H); 1.4 (m, 1H); MS (M+1) 363.0

Example 6

1-Methyl-1H-imidazole-4-carboxylic acid (3-aza-bicyclo[3.1.0]hex-6-ylmethyl)-(4-fluoro-3-isopropoxy-benzyl)-amide 100 MHz $^{13}$C NMR (CD$_3$OD) δ 19.44, 21.26, 21.78, 35.94, 49.72, 60.37, 72.27, 116.33, 120.59, 124.55, 126.54, 137.30, 146.35, 151.91, 154.35, 158.89, 171.74.

Example 7

1-Methyl-1H-imidazole-4-carboxylic acid (3-aza-bicyclo[3.1.0]hex-6-ylmethyl)-(3-cyclopentyloxy-4-fluoro-benzyl)-amide 100 MHz $^{13}$C NMR (CD$_3$OD) δ 19.45, 21.75, 23.71, 32.55, 33.25, 35.80, 49.64, 51.77, 60.36, 79.18, 81.06, 112.50, 116.16, 118.73, 120.05, 124.59, 126.51, 132.29, 133.54, 137.25, 146.44, 152.76 (d, J=248), 158.77, 171.74.

Example 8

1-Methyl-1H-imidazole-4-carboxylic acid (3-aza-bicyclo[3.1.0]hex-6-ylmethyl)-[3-(2,2-dimethyl-propoxy)-4-fluoro-benzyl]-amide 100 MHz $^{13}$C NMR (CD$_3$OD) δ 19.41, 21.74, 25.73, 31.79, 35.80, 49.68, 51.74, 79.03, 112.49, 114.60, 115.85, 120.02, 124.53, 126.51, 137.21, 148.05, 152.20 (d, J=245), 158.85.

Example 9

1-Methyl-1H-imidazole-4-carboxylic acid (3-aza-bicyclo[3.1.0]hex-6-ylmethyl)-(3-cyclohexyloxy-4-fluoro-benzyl)-amide 100 MHz $^{13}$C NMR (CD$_3$OD) δ 19.46, 21.73, 23.31, 25.49, 31.62, 35.79, 41.04, 49.56, 51.63, 52.51, 77.23, 116.52, 120.63, 124.59, 126.51, 129.48, 137.21, 151.02, 153.21 (d, J=245), 158.68.

Example 10

1-Methyl-1H-imidazole-4-carboxylic acid (3-aza-bicyclo[3.1.0]hex-6-ylmethyl)-[3-(2,2,2-trifluoro-1-trifluoromethyl-ethyl)-benzyl]-amide 400 MHz $^1$HNMR (CDCl$_3$) δ 7.5 (s, 1H); 7.2-7.4 (m, 5H); 5.4 (brs, 1H); 4.8 (brs, 1H); 3.9-4.1 (m, 2H); 3.6 (s, 3H); 3.3 (m, 1H); 2.6-3.0 (m, 4H); 1.2-1.3 (m, 2H); 0.8-0.9 (m, 1H); 100 MHz $^{13}$C NMR (CD$_3$OD) δ 17.70, 19.01, 21.63, 23.35, 28.55, 33.72, 47.53, 48.24, 49.23, 50.19, 51.74, 54.19 (h, J=29), 118.92, 121.71, 124.54, 126.54, 126.78, 127.34, 128.55, 129.40, 136.85, 138.26, 139.96, 164.28; MS (M+1) 461.

Example 11

1-Methyl-1H-imidazole-4-carboxylic acid (3-aza-bicyclo[3.1.0]hex-6-ylmethyl)-[3-(2,2,2-trifluoro-ethyl)-benzyl]-amide 400 MHz $^1$HNMR (CDCl$_3$) δ 7.5 (s, 1H); 7.1-7.3 (m, 5H); 5.4 (brs, 1H); 4.8 (brs, 1H); 3.9 (brs, 1H); 3.6 (m, 3H); 3.2-3.3 (m, 3H); 2.7-2.8 (m, 3H); 2.1-2.2 (m, 1H); 1.4 (m, 2H); 0.7-0.8 (m, 1H); 100 MHz $^{13}$C NMR (CD$_3$OD) δ 3.13, 17.34, 18.69, 23.82, 33.75, 40.26 (q, J=30), 47.64, 48.89, 49.54, 51.82, 53.66, 121.81, 124.57, 126.43, 127.33, 128.97, 129.42, 130.08, 130.46, 136.85, 138.46, 139.31, 164.29; MS (M+1) 393.0.

Example 12

1-Methyl-1H-imidazole-4-carboxylic acid (3-cyclopropylmethyl-3-aza-bicyclo[3.1.0]hex-6-ylmethyl)-(3-trifluoromethoxy-benzyl)-amide To a stirring solution of 1-Methyl-1H-imidazole-4-carboxylic acid (3-aza-bicyclo[3.1.0]hex-6-ylmethyl)-(3-trifluoromethoxy-benzyl)-amide Hydrochloride prepared above (0.8 gm, 1.9 mmol) in 18.5 mL of DCE at room temperature was added Cyclopropanecarbaldehyde (0.1 mL, 1.6 mmol) and NaHB(OAc)$_3$ (0.8 gm, 3.7 mmol). The reaction stirred at room temperature for 16 hours, was quenched by the addition of saturated NaHCO$_3$, and extracted with CH$_2$Cl$_2$. The combined organic layers were dried over anhydrous MgSO$_4$, filtered and concentrated under reduced pressure to yield the crude material, which was purified via flash chromatography with 5-30% MeOH/CH$_2$Cl$_2$. The product containing fractions were collected and concentrated to yield 1-Methyl-1H-imidazole-4-carboxylic acid (3-cyclopropylmethyl-3-aza-bicyclo[3.1.0]hex-6-ylmethyl)-(3-trifluoromethoxy-benzyl)-amide 0.5 gm. 400 MHz $^1$H NMR (CDCl$_3$) δ 7.5 (s, 1H), 7.3 (m, 2H) 7.2-7.0 (m, 3H), 5.5 (brs, 1H) 4.8 (brs, 1H), 4.0 (brs, 1H), 3.7 (s, 3H), 3.3 (brs, 1H), 3.0 (m, 2H), 2.2 (m, 4H), 1.5 (brs, 1H), 1.3 (m, 2H), 0.8 (m, 1H), 0.4 (m, 2H), 0.0 (m, 2H); MS (M+1) 449.3.

General Procedure for the Reductive Alkylation Preparation of Compounds of Formula IX To a stirring solution of 1.0 equiv. of a compound of formula (VIII) in 1,2-dichloroethane (0.1 M) at room temperature was added the appropriately substituted aldehyde or ketone reagent (1.0-1.5 equiv.), and sodium triacetoxyborohydride (2.0 equiv.). The reaction mixtures were stirred at room temperature for up to 24 hours. The mixtures were then quenched by the addition of saturated sodium bicarbonate solution and extracted with methylene chloride. The combined organic layers were dried over anhydrous MgSO$_4$ and concentrated under reduced pressure. If needed, the resulting crude material was purified by flash chromatography with 4% MeOH/CH$_2$Cl$_2$. The product containing fractions were collected and concentrated to yield the desired tertiary amines in 70-95% yield.

The following compounds were made using the above procedure of Example 12, starting with the appropriate starting amine of formula (VIII) and the appropriate aldehyde or ketone reagent.

Furthermore, pharmaceutically acceptable salts of the compounds listed below can be prepared as follows. To a stirring solution of compounds of the general formula (IX) (prepared as described above in Example 1 and Example 12, 1.0 equiv.) in a suitable solvent such as ethyl acetate, dioxane, diethyl ether, methyl ethyl ketone, methylene chloride/methanol (1:1) or methanol (0.1 M) at room temperature was added the appropriate acid, such as hydrochloric acid, citric acid, trifluoroacetic acid, p-toluenesulfonic acid, methanesulfonic acid or benzene sulfonic acid (2-3 equiv) in one portion. The resulting mixture was stirred at room temperature for up to 18 hours, then concentrated under reduced pressure to afford the desired salts.

Example 13

1-Methyl-1H-imidazole-4-carboxylic acid (3-cyclopentylmethyl-3-aza-bicyclo[3.1.0]hex-6-ylmethyl)-(3-trifluoromethoxy-benzyl)-amide 400 MHz $^1$H NMR (CDCl$_3$) δ 7.5 (m, 1H), 7.3-7.0 (m, 5H), 5.5 (brs, 1H) 4.8 (brs, 1H), 4.0 (brs, 1H), 3.7 (s, 3H), 3.3 (brs, 1H), 2.9-2.8 (m, 2H), 2.19 (m, 4H), 1.8 (brs, 1H), 1.6-1.1 (m, 10H); MS (M+1) 477.3.

Example 14

1-Methyl-1H-imidazole-4-carboxylic acid (3-trifluoromethoxy-benzyl)-[3-(4-trifluoromethoxy-benzyl)-3-aza-bicyclo[3.1.0]hex-6-ylmethyl]-amide 400 MHz $^1$H NMR (CDCl$_3$) δ 7.5 (s, 1H), 7.5-7.0 (m, 9H), 5.5 (brs, 1H) 4.8 (brs, 1H), 4.0 (brs, 1H), 3.7 (s, 3H), 3.5-3.4 (m, 2H), 3.3 (m, 1H), 2.8-2.7 (m, 2H), 2.2 (brs, 2H), 1.4 (brs, 1H), 1.2 (brs, 2H); MS (M+1) 569.5.

Example 15

1-Methyl-1H-imidazole-4-carboxylic acid (3-chloro-benzyl)-(3-cyclopropylmethyl-3-aza-bicyclo[3.1.0]hex-6-ylmethyl)-amide 400 MHz $^1$H NMR (CDCl$_3$) δ 7.5 (m, 1H), 7.3-7.2 (m, 5H), 5.4 (brs, 1H) 4.8 (brs, 1H), 4.0 (brs, 1H), 3.7 (s, 3H), 3.3 (brs, 1H), 3.0 (brs, 1H), 2.2 (brs, 4H), 1.7 (brs, 2H), 1.4 (brs, 1H), 1.3 (brs, 2H), 0.4 (m, 2H), 0.0 (m, 2H); MS (M+1) 399.3.

Example 16

Methyl-1H-imidazole-4-carboxylic acid (3-chloro-benzyl)-(3-cyclopentylmethyl-3-aza-bicyclo[3.1.0]hex-6-ylmethyl)-amide 400 MHz $^1$H NMR (CDCl$_3$) δ 7.6 (m, 1H), 7.3-7.2 (m, 5H), 5.4 (brs, 1H) 4.8 (brs, 1H), 3.9 (brs, 1H), 3.7 (brs, 3H), 3.3 (m, 1H), 2.9 (m, 2H), 2.2 (m, 3H), 1.9-1.1 (m, 13H); MS (M+1) 427.4.

Example 17

1-Methyl-1H-imidazole-4-carboxylic acid (3-chloro-benzyl)-[3-(4-trifluoromethoxy-benzyl)-3-aza-bicyclo[3.1.0]hex-6-ylmethyl]-amide 400 MHz $^1$H NMR (CDCl$_3$) δ 7.6 (d, 1H), 7.5-7.1 (m, 9H), 5.4 (brs, 1H), 4.8 (brs, 1H), 4.0 (brs, 1H), 3.7 (s, 3H), 3.5 (brs, 2H), 3.3 (d, 1H), 2.8 (m, 2H), 2.2 (m, 2H), 1.40 (brs, 1H), 1.2 (brs, 2H); MS (M+1) 519.4.

Example 18

1-Methyl-1H-imidazole-4-carboxylic acid (3-cyclopropylmethyl-3-aza-bicyclo[3.1.0]hex-6-ylmethyl)-(3-trifluoromethyl-benzyl)-amide 400 MHz $^1$H NMR (CDCl$_3$) δ 7.6-7.4 (m, 6H), 5.4 (brs, 1H) 4.8 (brs, 1H), 3.9-3.7 (m, 5H), 3.0 (m, 2H), 2.9 (m, 2H), 2.4 (brs, 2H), 1.8 (m, 2H), 1.4 (m, 2H), 0.7 (m, 2H), 0.4-0.3 (m, 2H); MS (M+1) 433.3.

Example 19

1-Methyl-1H-imidazole-4-carboxylic acid (3-ethyl-3-aza-bicyclo[3.1.0]hex-6-ylmethyl)-(4-fluoro-3-trifluoromethyl-benzyl)-amide 400 MHz 1HNMR (CDCl$_3$) δ 7.5-7.6 (m, 3H), 7.3 (s, 1H); 7.1 (t, J=9.3, 1H), 5.4 (brs, 1H), 4.8 (brs, 1H), 4.0 (brs, 1H), 3.7 (s, 3H), 3.3 (brs, 1H), 2.2-3.0 (m, 4H), 1.0-1.7 (m, 8H).

Example 20

1-Methyl-1H-imidazole-4-carboxylic acid (4-fluoro-3-trifluoromethyl-benzyl)-(3-methyl-3-aza-bicyclo[3.1.0]hex-6-ylmethyl)-amide 400 MHz 1HNMR (CDCl$_3$) δ 7.5-7.6 (m, 3H); 7.3 (s, 1H); 7.1 (t, J=9.3, 1H); 5.4 (brs, 1H); 4.8 (brs, 1H); 4.0 (brs, 1H); 3.6-3.7 (m, 3H); 3.3 (brs, 1H); 2.8-3.1 (brs, 2H); 2.3 (brs, 5H); 1.2-1.4 (m, 3H).

Example 21

1-Methyl-1H-imidazole-4-carboxylic acid (3-chloro-benzyl)-(3-ethyl-3-aza-bicyclo[3.1.0]hex-6-ylmethyl)-amide 400 MHz 1HNMR (CDCl$_3$) δ 7.5 (m, 1H); 7.1-7.3 (m, 5H); 5.4 (brs, 1H); 4.8 (brs, 1H); 4.0 (brs, 1H); 3.7 (m, 3H); 3.3 (brs, 1H); 3.0 (brs, 2H); 2.1-2.4 (m, 4H); 1.2-1.4 (m, 3H); 0.9-1.0 (m, 3H).

Example 22

1-Methyl-1H-imidazole-4-carboxylic acid (3-ethyl-3-aza-bicyclo[3.1.0]hex-6-ylmethyl)-(3-trifluoromethoxy-benzyl)-amide Hydrochloride 400 MHz 1HNMR (CD$_3$OD) δ 7.6 (m, 2H); 7.1-7.4 (m, 4H); 5.3 (brs, 1H); 4.8 (brs, 1H); 3.8 (brs, 1H); 3.7 (brs, 3H); 3.3 (brs, 1H); 2.8 (brs, 2H); 2.3-2.5 (m, 4H); 1.3 (brs, 3H); 1.0 (m, 3H).

Example 23

1-Methyl-1H-imidazole-4-carboxylic acid (3-methyl-3-aza-bicyclo[3.1.0]hex-6-ylmethyl)-(3-trifluoromethoxy-benzyl)-amide 400 MHz 1HNMR (CDCl3) δ 7.5 (m, 1H); 7.1-7.3 (m, 5H); 5.5 (brs, 1H); 4.8 (brs, 1H); 4.0 (brs, 1H); 3.7 (brs, 3H); 3.3 (brs, 1H); 2.9 (brs, 2H); 2.2 (brs, 5H); 1.3-1.4 (m, 3H).

Example 24

1-Methyl-1H-imidazole-4-carboxylic acid (3-ethyl-3-aza-bicyclo[3.1.0]hex-6-ylmethyl)-(3-trifluoromethyl-benzyl)-amide 400 MHz $^1$HNMR (CDCl$_3$) δ 7.6 (m, 1H); 7.3-7.5 (m, 5H); 5.5 (brs, 1H); 4.9 (brs, 1H); 4.0 (brs, 1H); 3.6-3.7 (m, 3H); 3.3 (brs, 1H); 3.0 (brs, 2H); 2.0-2.4 (m, 4H); 1.2-1.5 (m, 3H); 1.0 (brs, 3H).

Example 25

1-Methyl-1H-imidazole-4-carboxylic acid (3-methyl-3-aza-bicyclo[3.1.0]hex-6-ylmethyl)-(3-trifluoromethyl-benzyl)-amide 400 MHz $^1$HNMR (CDCl$_3$) δ 7.3-7.6 (m, 6H); 5.5 (brs, 1H); 4.8 (brs, 1H); 4.0 (brs, 1H); 3.6-3.7 (m, 3H); 3.3 (brs, 1H); 3.0 (m, 2H); 2.3 (m, 5H); 1.3-1.7 (m, 3H).

Example 26

1-Methyl-1H-imidazole-4-carboxylic acid (3,5-dichloro-benzyl)-(3-methyl-3-aza-bicyclo[3.1.0]hex-6-ylmethyl)-amide 400 MHz $^1$HNMR (CDCl$_3$) δ 7.6 (m, 1H); 7.3 (brs, 1H); 7.1-7.2 (m, 3H); 5.4 (brs, 1H); 4.7 (brs, 1H); 4.0 (brs, 1H); 3.7 (brs, 3H); 3.3 (brs, 1H); 2.9 (brs, 2H); 2.3 (brs, 5H); 1.2-1.4 (m, 3H).

Example 27

1-Methyl-1H-imidazole-4-carboxylic acid (3,5-dichloro-benzyl)-(3-ethyl-3-aza-bicyclo[3.1.0]hex-6-ylmethyl)-amide Hydrochloride 400 MHz $^1$HNMR (CD$_3$OD) δ 9.0 (s, 1H); 8.3 (brs, 1H) 7.3-7.4 (m, 3H); 4.8 (brs, 2H); 4.0-4.1 (m, 4H); 3.5-3.6 (m, 5H); 3.1-3.2 (m, 2H); 1.8 (m, 3H); 1.2-1.3 (m, 3H).

Example 28

1-Methyl-1H-imidazole-4-carboxylic acid (3-chloro-4-fluoro-benzyl)-(3-methyl-3-aza-bicyclo[3.1.0]hex-6-ylmethyl)-amide 400 MHz $^1$HNMR (CDCl$_3$) δ 7.52 (s, 1H), 7.28 (m, 2H), 7.11 (m, 1H), 7.00 (t, J=8, 1H), 4.67 and 5.355 (m, 2H), 3.65 (s, 3H), 3.24 and 3.925 (m, 2H), 2.86 (m, 2H), 2.19 (s, 5H), 1.36 (m, 1H), 1.26 (m, 2H); MS (M+1) 377.1. 100 MHz $^{13}$C-NMR (CDCl$_3$, δ): 18.375, 19.616, 22.763, 33.791, 41.499, 47.025, 48.355, 49.522, 50.112, 57.133, 116.5785 (d, J=21), 120.929, 126.724, 127.576, 129.789, 135.7, 136.742, 138.432, 157.325 (d, J=248), 164.039.

Example 29

1-Methyl-1H-imidazole-4-carboxylic acid (3-chloro-4-fluoro-benzyl)-(3-ethyl-3-aza-bicyclo[3.1.0]hex-6-ylmethyl)-amide 400 MHz $^1$HNMR (CD$_3$OD) δ 9.0 (s, 1H); 8.2-8.3 (m, 1H) 7.5 (s, 1H); 7.3 (m, 2H); 4.8 (brs, 2H); 3.8-4.0 (m, 4H); 3.4-3.6 (m, 4H); 3.1-3.3 (m, 2H); 1.6-1.8 (m, 3H); 1.3 (m, 3H).

Example 30

1-Methyl-1H-imidazole-4-carboxylic acid (3-chloro-benzyl)-(3-methyl-3-aza-bicyclo[3.1.0]hex-6-ylmethyl)-amide 400 MHz $^1$HNMR (CDCl$_3$) δ 7.6 (s, 1H); 7.2-7.3 (m, 5H); 5.4 (brs, 1H); 4.8 (brs, 1H); 4.0 (brs, 1H); 3.7 (s, 3H); 3.3 (brs, 1H); 3.0 (brs, 2H); 2.2-2.3 (m, 5H); 1.3-1.5 (m, 3H).

Example 31

1-Methyl-1H-imidazole-4-carboxylic acid (3-azetidin-3-yl-3-aza-bicyclo[3.1.0]hex-6-ylmethyl)-(3-trifluoromethoxy-benzyl)-amide 100 MHz $^{13}$C-NMR (CDCl$_3$) δ 15.45, 19.4, 21.79, 33.88, 42.10, 47.56, 50.31, 50.75, 53.10, 119.33, 119.67, 120.23, 121.89, 126.22, 128.62, 129.09, 130.10, 137.13, 137.75, 141.29, 149.63, 164.38.

Example 32

1-Methyl-1H-imidazole-4-carboxylic acid (2,4-dichloro-benzyl)-(3-methyl-3-aza-bicyclo[3.1.0]hex-6-ylmethyl)-amide 400 MHz $^1$HNMR (CDCl3) δ 7.6 (brs, 1H); 7.2 (m, 3H); 7.1 (m, 1H); 5.5 (brs, 1H); 4.8 (brs, 1H); 4.1 (brs, 1H); 3.7 (brs, 3H); 3.3 (brs, 1H); 2.9 (brs, 2H); 2.2 (brs, 5H); 1.3-1.4 (m, 3H); MS (M+1) 393.0.

Example 33

1-Methyl-1H-imidazole-4-carboxylic acid (2,4-dichloro-benzyl)-(3-ethyl-3-aza-bicyclo[3.1.0]hex-6-ylmethyl)-amide 400 MHz $^1$HNMR (CDCl$_3$) δ 7.6 (brs, 1H); 7.2-7.4 (m, 3H); 7.1 (m, 1H); 5.5 (brs, 1H); 4.8 (brs, 1H); 4.1 (brs, 1H); 3.6-3.7 (m, 3H); 3.3 (brs, 1H); 2.9-3.0 (m, 2H); 2.4 (m, 2H); 2.2 (m, 2H); 1.3-1.4 (m, 3H); 0.9-1.0 (m, 3H); MS (M+1) 407.0.

Example 34

1-Methyl-1H-imidazole-4-carboxylic acid (3,4-dichloro-benzyl)-(3-methyl-3-aza-bicyclo[3.1.0]hex-6-ylmethyl)-amide 400 MHz $^1$HNMR (CDCl$_3$) δ 7.6 (m, 1H); 7.3-7.4 (m, 3H); 7.1 (brs, 1H); 5.4 (brs, 1H); 4.7 (brs, 1H); 4.0 (brs, 1H); 3.6 (brs, 3H); 3.3 (brs, 1H); 3.0 (brs, 2H); 2.2-2.3 (m, 5H); 1.2-1.4 (m, 3H).

Example 35

1-Methyl-1H-imidazole-4-carboxylic acid (3,4-dichloro-benzyl)-(3-ethyl-3-aza-bicyclo[3.1.0]hex-6-ylmethyl)-amide 400 MHz $^1$HNMR (CDCl$_3$) δ 7.6 (s, 1H); 7.3-7.4 (m, 3H); 7.1 (brs, 1H); 5.4 (brs, 1H); 4.7 (brs, 1H); 4.0 (brs, 1H); 3.7 (s, 3H); 3.3 (brs, 1H); 3.0 (brs, 2H); 2.2-2.4 (m, 4H); 1.2-1.4 (m, 3H); 1.0 (brs, 3H).

Example 36

1-Methyl-1H-imidazole-4-carboxylic acid [3-(1-methanesulfonyl-azetidin-3-yl)-3-aza-bicyclo[3.1.0]hex-6-ylmethyl]-(3-trifluoromethoxy-benzyl)-amide 100 MHz $^{13}$C-NMR (CDCl$_3$) δ 18.42, 19.70, 21.98, 33.84, 35.62, 47.70, 49.72, 50.69, 51.21, 54.75, 112.50, 119.55, 120.30, 125.98, 126.72, 129.95, 136.82, 138.39, 149.61, 164.17.

Example 37

1-Methyl-1H-imidazole-4-carboxylic acid (3-azetidin-3-yl-3-aza-bicyclo[3.1.0]hex-6-ylmethyl)-(4-fluoro-3-trifluoromethyl-benzyl)-amide 100 MHz $^{13}$C-NMR (CDCl$_3$) δ 18.30, 19.62, 22.02, 22.09, 33.78, 47.55, 48.73, 49.93, 50.67, 51.28, 51.57, 53.06, 53.45, 56.49, 57.66, 117.01 (d, J=21), 121.40, 124.11, 126.28, 126.32, 126.74, 133.23, 135.19, 136.85, 138.12, 158.93 (d, J=255), 164.02; MS(M+1) 452.2.

Example 38

1-Methyl-1H-imidazole-4-carboxylic acid (3-azetidin-3-yl-3-aza-bicyclo[3.1.0]hex-6-ylmethyl)-(3-chloro-4-fluoro-benzyl)-amide 100 MHz $^{13}$C-NMR (CDCl$_3$) δ 18.29, 19.56, 21.99, 33.83, 47.44, 48.52, 49.69, 50.31, 50.58, 51.29, 51.52, 56.37, 116.59 (d, J=21), 126.62, 127.44, 129.75, 135.85, 136.90, 138.08, 157.29 (d, J=245), 164.10; MS (M+1) 418.2.

Example 39

1-Methyl-1H-imidazole-4-carboxylic acid (4-fluoro-3-trifluoromethyl-benzyl)-[3-(1-methyl-azetidin-3-yl)-3-aza-bicyclo[3.1.0]hex-6-ylmethyl]-amide 100 MHz $^{13}$C-NMR (CDCl$_3$) δ 18.40, 19.65, 22.15, 33.84, 46.09, 47.66, 48.95, 50.70, 51.82, 52.97, 61.05, 116.92, 117.12, 126.33, 126.90, 133.29, 136.79; MS (M+1) 466.2.

Example 40

1-Methyl-1H-imidazole-4-carboxylic acid (3-chloro-4-fluoro-benzyl)-[3-(1-methyl-azetidin-3-yl)-3-aza-bicyclo[3.1.0]hex-6-ylmethyl]-amide 100 MHz $^{13}$C-NMR (CDCl$_3$) δ 18.43, 22.11, 33.85, 45.95, 47.55, 49.71, 50.61, 51.84, 52.89, 61.00, 74.97, 116.50, 116.71, 126.82, 127.71, 129.93, 136.85; MS (M+1) 464.2.

Example 41

1-Methyl-1H-imidazole-4-carboxylic acid (3-azetidin-3-yl-3-aza-bicyclo[3.1.0]hex-6-ylmethyl)-(3-trifluoromethyl-benzyl)-amide 100 MHz $^{13}$C-NMR (CDCl$_3$) δ 21.84, 22.02, 25.90, 33.88, 47.17, 50.31, 50.79, 51.53, 52.50, 53.19, 57.37, 124.36, 126.69, 129.14, 131.04, 136.84, 161.09, 164.25; MS (M+1) 434.1.

Example 42

1-Methyl-1H-imidazole-4-carboxylic acid [3-(1-methyl-azetidin-3-yl)-3-aza-bicyclo[3.1.0]hex-6-ylmethyl]-(3-trifluoromethyl-benzyl)-amide 100 MHz $^{13}$C-NMR (CDCl$_3$) δ 18.41, 19.72, 22.14, 33.83, 45.86, 47.75, 49.23, 49.90, 51.33, 51.79, 52.82, 60.96, 124.05, 124.40, 126.74, 129.07, 131.01, 136.82, 164.17; MS (M+1) 448.4.

Example 43

1-Methyl-1H-imidazole-4-carboxylic acid (3-chloro-benzyl)-[3-(1-methyl-azetidin-3-yl)-3-aza-bicyclo[3.1.0]hex-6-ylmethyl]-amide 100 MHz $^{13}$C-NMR (CDCl$_3$) δ 18.43, 19.66, 22.12, 33.82, 46.02, 47.59, 48.97, 51.12, 51.82, 52.89, 61.06, 126.03, 126.67, 127.35, 127.67, 129.86, 134.50, 136.81, 138.55, 164.08; MS MS (M+1) 414.2.

Example 44

1-Methyl-1H-imidazole-4-carboxylic acid (3-methyl-3-aza-bicyclo[3.1.0]hex-6-ylmethyl)-[3-(2,2,2-trifluoro-ethyl)-benzyl]-amide 400 MHz $^1$HNMR (CDCl$_3$) δ 7.5 (s, 1H); 7.1-7.3 (m, 5H); 5.4 (brs, 1H); 4.8 (brs, 1H); 3.9 (brs, 1H); 3.6 (s, 3H); 3.2-3.3 (m, 3H); 2.9 (brs, 2H); 2.2 (m, 5H); 1.4 (m, 1H); 1.2-1.3 (m, 2H); 100 MHz $^{13}$C-NMR (CDCl$_3$) δ 18.47, 19.64, 22.73, 33.74, 40.31 (q, J=29), 41.50, 46.87, 48.76, 49.22, 50.87, 57.17, 121.87, 124.59, 126.38, 127.34, 128.96, 129.40, 130.45, 136.73, 138.60, 139.32, 164.20; MS (M+1) 407.1.

Example 45

1-Methyl-1H-imidazole-4-carboxylic acid (3-methyl-3-aza-bicyclo[3.1.0]hex-6-ylmethyl)-[3-(2,2,2-trifluoro-1-trifluoromethyl-ethyl)-benzyl]-amide 400 MHz $^1$HNMR (CDCl$_3$) δ 7.5 (s, 1H); 7.2-7.4 (m, 5H); 5.4 (brs, 1H); 4.8 (brs, 1H); 3.9-4.0 (m, 2H); 3.6 (s, 3H); 3.3 (brs, 1H); 2.8 (m, 2H); 2.2 (m, 5H); 1.4 (m, 1H); 1.2 (m, 2H); 100 MHz $^{13}$C-NMR (CDCl$_3$) δ 18.44, 19.62, 22.76, 33.72, 41.43, 47.09, 48.85, 49.50, 50.88, 54.37 (h, J=29), 57.09, 118.94, 121.71, 124.51, 126.48, 126.70, 127.33, 128.26, 129.39, 136.73, 138.51, 139.70, 164.22; MS (M+1) 475.1.

Example 46

1-Methyl-1H-imidazole-4-carboxylic acid [3-(1-hydroxy-cyclohexylmethyl)-3-aza-bicyclo[3.1.0]hex-6-ylmethyl]-(3-trifluoromethoxy-benzyl)-amide Methylenecyclohexane epoxide was added to a 15 mL round bottomed flask under nitrogen, followed by ethanol (3.3 mL), triethylamine (0.097 mL, 0.696 mmol), and 1-Methyl-1H-imidazole-4-carboxylic acid (3-aza-bicyclo[3.1.0]hex-6-ylmethyl)-(3-trifluoromethoxy-benzyl)-amide hydrochloride (0.100 g, 0.232 mmol). The reaction warmed to 60° C., then refluxed for 4.5 hours and then cooled to room temperature. The reaction was then quenched with saturated sodium bicarbonate solution and extracted twice with methylene chloride. The combined organic layers were dried (MgSO$_4$), filtered, and concentrated in vacuo to give 0.087 g of 1-Methyl-1H-imidazole-4-carboxylic acid [3-(1-hydroxy-cyclohexylmethyl)-3-aza-bicyclo[3.1.0]hex-6-ylmethyl]-(3-trifluoromethoxy-benzyl)-amide. 400 MHz $^1$H NMR (CDCl$_3$) δ 7.6 (s, 1H), 7.0-7.3 (m, 5H), 5.4 (brs, 1H), 4.8 (brs, 1H), 4.0 (brs, 1H), 3.7 (s, 3H), 3.3 (brs, 1H), 2.9-3.0 (m, 2H), 2.4-2.5 (m, 2H), 2.3 (m, 2H), 1.2-1.8 (m, 13H); MW (M+1) 507.1

Other examples prepared according to the procedure for Example 46 described above include:

Example 47

1-Methyl-1H-imidazole-4-carboxylic acid {3-[2-(2-chloro-phenyl)-2-hydroxy-ethyl]-3-aza-bicyclo[3.1.0]hex-6-ylmethyl}-(3-trifluoromethoxy-benzyl)-amide 400 MHz $^1$H NMR (CDCl$_3$) δ 7.6 (d, J=1.24 Hz, 1H), 7.1-7.4 (m, 9H), 5.5 (brs, 1H), 4.8 (brs, 1H), 4.5 (brs, 1H), 4.0 (brs, 1H), 3.7 (s, 3H), 3.3 (brs, 1H), 2.8-3.2 (m, 2H), 2.1-2.6 (m, 4H), 1.2-1.6 (m, 3H); MW (M+1) 549.3.

Example 48

1-Methyl-1H-imidazole-4-carboxylic acid [3-(1-hydroxy-cyclopentylmethyl)-3-aza-bicyclo[3.1.0]hex-6-ylmethyl]-(3-trifluoromethoxy-benzyl)-amide 400 MHz $^1$H NMR (CDCl$_3$) δ 7.6 (d, J=1.7 Hz, 1H), 7.3 (t, J=7.9 Hz, 2H), 7.1-7.2 (m, 2H), 7.1 (d, J=8.3 Hz, 1H), 5.5 (brs, 1H), 4.8 (brs, 1H), 4.0 (brs, 1H), 3.7 (s, 3H), 3.3 (brs, 2H), 3.0 (m, 2H), 2.4-2.5 (m, 4H), 1.7-1.8 (m, 2H), 1.4-1.6 (m, 6H), 1.3-1.4 (m, 3H); MW (M+1) 493.3.

Preparation 5

Benzyl 2-(6-((N-(3-(trifluoromethoxy)benzyl)-1-methyl-1H-imidazole-4-carboxamido)methyl)-3-aza-bicyclo[3.1.0]hexan-3-yl)acetate To a stirring solution of 6-{[(1-Methyl-1H-imidazole-4-carbonyl)-(3-trifluoromethoxy-benzyl)-amino]-methyl}-3-aza-bicyclo[3.1.0]hexane-3-carboxylic acid tert-butyl ester prepared above (2.63 gm, 5.63 mmol) in 30 mL DMF was added potassium carbonate (3.89 gm, 28.2 mmol), tetraethylammonium chloride (150 mg), followed by benzyl 2-bromoacetate (0.88 mL, 5.63 mmol). The reaction was stirred at room temperature for 20 hours and quenched with water. The mixture was diluted with ethyl acetate, the layers separated and the aqueous layer extracted three times with ethyl acetate. The combined organic layers were dried over anhydrous sodium sulfate, filtered and concentrated to yield 2.8 gm of crude material. The crude material was purified by flash chromatography to yield 2.7 gm of benzyl 2-(6-((N-(3-(trifluoromethoxy)benzyl)-1-methyl-1H-imidazole-4-carboxamido)methyl)-3-aza-bicyclo[3.1.0]hexan-3-yl)acetate; MS (M+1) 543.3.

Preparation 6

2-(6-((N-(3-(trifluoromethoxy)benzyl)-1-methyl-1H-imidazole-4-carboxamido)methyl)-3-aza-bicyclo[3.1.0]hexan-3-yl)acetic acid To a par bottle charged with benzyl 2-(6-((N-(3-(trifluoromethoxy)benzyl)-1-methyl-1H-imidazole-4-carboxamido)methyl)-3-aza-bicyclo[3.1.0]hexan-3-yl)acetate (2.7 gm, 5.07 mmol) in 80 mL $CH_3OH$, was added 300 mg palladium hydroxide on carbon (20%). The mixture was hydrogenated under 40 psi $H_2$ at room temperature for 1 hour. The mixture was filtered over a celite, the celite pad was washed with $CH_3OH$ and the resulting solution was concentrated to yield 2.3 gm of 2-(6-((N-(3-(trifluoromethoxy)benzyl)-1-methyl-1H-imidazole-4-carboxamido)methyl)-3-aza-bicyclo[3.1.0]hexan-3-yl)acetic acid as a yellow solid; 400 MHz $^1H$ NMR ($CDCl_3$) δ 7.54 (s, 1H), 7.23-7.33 (m, 3H), 7.15 (s, 1H), 7.05 (d, J=7.9 Hz, 1H), 5.4 (brs, 2H), 4.81 (brs, 1H), 3.96 (brs, 1H), 3.68 (s, 3H), 3.49 (s, 2H), 3.28 (brs, 1H), 3.12 (brs, 2H), 1.76 (brs, 1H), 1.66 (brs, 2H); MS (M+1) 452.1.

General Procedure for Amide Couplings

A solution of 2-(6-((N-(3-(trifluoromethoxy)benzyl)-1-methyl-1H-imidazole-4-carboxamido)methyl)-3-aza-bicyclo[3.1.0]hexan-3-yl)acetic acid prepared above (1.0 equiv.) in 1,2-dichloroethane/triethylamine/dimethylformamide solution was added to the amines (1.9 equiv.), followed by HBTU (2.1 equiv). The reactions stirred at room temperature overnight, quenched with 1N NaOH and extracted with dichloromethane. The combined organic layers were dried and concentrated to yield the crude amides that were further purified by flash chromatography or HPLC.

Alternatively, amides could be prepared by utilizing a parallel library synthesis procedure as described below.

Two dram vials were charged with amines (0.075 mmole, 1.875 eq.). 2-(6-((N-(3-(trifluoromethoxy)benzyl)-1-methyl-1H-imidazole-4-carboxamido)methyl)-3-aza-bicyclo[3.1.0]hexan-3-yl)acetic acid was taken up in DCE/TEA/DMF (500/14/100) and was added as a cloudy suspension (0.04 mmol., 18.1 mg, 1.0 eq. per 0.614 ml DCE/TEA/DMF, 1.0 eq. DIEA). Add HBTU (31.3 mg, 0.0825 mmol, 2.06 eq) dissolved in 0.2 ml of DMF. Shake at room temperature overnight. Aliquot samples for LC MS analysis. Add 1.5 ml 1 N NaOH and 2.5 ml DCM. Vortex and remove the organic layer and load onto a SCX SPE (6 ml, 1 g, Silicycle brand). Repeat extraction 2 times. Elute SCX SPE with 5 ml DCM, then 5 ml MeOH. Switch to tarred collection vials and elute with 1 N TEA in MeOH (7.5 ml). Dry down. Weigh and prepare TFA salt (15/485 TFA/DCM). Dry down. Purification by HPLC/MS.

Other representative examples prepared according to the procedures and examples described above include:

| Example | MW Calc | Mass Spec Data (M + 1) | IUPAC Name |
|---|---|---|---|
| 49 | 378.1 | 379.27 | 1-Methyl-1H-imidazole-4-carboxylic acid (3-aza-bicyclo[3.1.0]hex-6-ylmethyl)-(3,4-dichloro-benzyl)-amide |
| 50 | 378.17 | 379.31 | 1-Methyl-1H-imidazole-4-carboxylic acid (3-aza-bicyclo[3.1.0]hex-6-ylmethyl)-(2-trifluoromethyl-benzyl)-amide |
| 51 | 396.16 | 397.43 | 1-Methyl-1H-imidazole-4-carboxylic acid (3-aza-bicyclo[3.1.0]hex-6-ylmethyl)-(3-fluoro-5-trifluoromethyl-benzyl)-amide |
| 52 | 378.17 | 379.29 | 1-Methyl-1H-imidazole-4-carboxylic acid (3-aza-bicyclo[3.1.0]hex-6-ylmethyl)-(3-trifluoromethyl-benzyl)-amide |
| 53 | 378.17 | 379.29 | 1-Methyl-1H-imidazole-4-carboxylic acid (3-aza-bicyclo[3.1.0]hex-6-ylmethyl)-(3-trifluoromethyl-benzyl)-amide |
| 54 | 378.1 | 379.27 | 1-Methyl-1H-imidazole-4-carboxylic acid (3-aza-bicyclo[3.1.0]hex-6-ylmethyl)-(2,3-dichloro-benzyl)-amide |
| 55 | 378.1 | 379.25 | 1-Methyl-1H-imidazole-4-carboxylic acid (3-aza-bicyclo[3.1.0]hex-6-ylmethyl)-(2,4-dichloro-benzyl)-amide |
| 56 | 394.16 | 395.35 | 1-Methyl-1H-imidazole-4-carboxylic acid (3-aza-bicyclo[3.1.0]hex-6-ylmethyl)-(2-trifluoromethoxy-benzyl)-amide |
| 57 | 396.16 | 397.37 | 1-Methyl-1H-imidazole-4-carboxylic acid (3-aza-bicyclo[3.1.0]hex-6-ylmethyl)-(4-fluoro-3-trifluoromethyl-benzyl)-amide |
| 58 | 396.16 | 397.37 | 1-Methyl-1H-imidazole-4-carboxylic acid (3-aza-bicyclo[3.1.0]hex-6-ylmethyl)-(2-fluoro-5-trifluoromethyl-benzyl)-amide |
| 59 | 338.21 | 339.4 | 1-Methyl-1H-imidazole-4-carboxylic acid (3-aza-bicyclo[3.1.0]hex-6-ylmethyl)-(3-phenyl-propyl)-amide |
| 60 | 402.21 | 403.4 | 1-Methyl-1H-imidazole-4-carboxylic acid (3-aza-bicyclo[3.1.0]hex-6-ylmethyl)-(4-phenoxy-benzyl)-amide |
| 61 | 386.21 | 387.45 | 1-Methyl-1H-imidazole-4-carboxylic acid (3-aza-bicyclo[3.1.0]hex-6-ylmethyl)-biphenyl-4-ylmethyl-amide |
| 62 | 352.23 | 353.42 | 1-Methyl-1H-imidazole-4-carboxylic acid (3-aza-bicyclo[3.1.0]hex-6-ylmethyl)-(4-phenyl-butyl)-amide |
| 63 | 391.15 | 392.45 | Pyridine-2-carboxylic acid (3-aza-bicyclo[3.1.0]hex-6-ylmethyl)-(3-trifluoromethoxy-benzyl)-amide |
| 64 | 386.21 | 387.43 | 1-Methyl-1H-imidazole-4-carboxylic acid (3-aza-bicyclo[3.1.0]hex-6-ylmethyl)-biphenyl-3-ylmethyl-amide |
| 65 | 393.15 | 394.37 | Pyridine-2-carboxylic acid (3-aza-bicyclo[3.1.0]hex-6-ylmethyl)-(4-fluoro-3-trifluoromethyl-benzyl)-amide |
| 66 | 393.15 | 394.39 | Pyridine-2-carboxylic acid (3-aza-bicyclo[3.1.0]hex-6-ylmethyl)-(5-fluoro-2-trifluoromethyl-benzyl)-amide |
| 67 | 381.11 | 381.67 | Thiazole-4-carboxylic acid (3-aza-bicyclo[3.1.0]hex-6-ylmethyl)-(3-trifluoromethyl-benzyl)-amide |
| 68 | 393.15 | 394.44 | Pyridine-2-carboxylic acid (3-aza-bicyclo[3.1.0]hex-6-ylmethyl)-(2-fluoro-5-trifluoromethyl-benzyl)-amide |
| 69 | 393.15 | 394.4 | Pyridine-2-carboxylic acid (3-aza-bicyclo[3.1.0]hex-6-ylmethyl)-(3-fluoro-5-trifluoromethyl-benzyl)-amide |
| 70 | 397.11 | 398.37 | Thiazole-4-carboxylic acid (3-aza-bicyclo[3.1.0]hex-6-ylmethyl)-(2-trifluoromethoxy-benzyl)-amide |
| 71 | 381.11 | 382.36 | Thiazole-4-carboxylic acid (3-aza-bicyclo[3.1.0]hex-6-ylmethyl)-(2-trifluoromethyl-benzyl)-amide |
| 72 | 397.11 | 398.38 | Thiazole-4-carboxylic acid (3-aza-bicyclo[3.1.0]hex-6-ylmethyl)-(3-trifluoromethoxy-benzyl)-amide |
| 73 | 358.16 | 359.41 | 1-Methyl-1H-imidazole-4-carboxylic acid (3-aza-bicyclo[3.1.0]hex-6-ylmethyl)-[2-(4-chloro-phenyl)-ethyl]-amide |
| 74 | 392.18 | 393.47 | 1-Methyl-1H-imidazole-4-carboxylic acid (3-aza-bicyclo[3.1.0]hex-6-ylmethyl)-[2-(3-trifluoromethyl-phenyl)-ethyl]-amide |
| 75 | 349.11 | 350.44 | Thiazole-4-carboxylic acid (3-aza-bicyclo[3.1.0]hex-6-ylmethyl)-(2,4-difluoro-benzyl)-amide |

-continued

| Example | MW Calc | Mass Spec Data (M + 1) | IUPAC Name |
|---|---|---|---|
| 76 | 358.16 | 359.4 | 1-Methyl-1H-imidazole-4-carboxylic acid (3-aza-bicyclo[3.1.0]hex-6-ylmethyl)-[2-(3-chloro-phenyl)-ethyl]-amide |
| 77 | 450.22 | 451.16 | 1-Methyl-1H-imidazole-4-carboxylic acid (3-isobutyl-3-aza-bicyclo[3.1.0]hex-6-ylmethyl)-(3-trifluoromethoxy-benzyl)-amide |
| 78 | 464.24 | 465.18 | 1-Methyl-1H-imidazole-4-carboxylic acid [3-(2,2-dimethyl-propyl)-3-aza-bicyclo[3.1.0]hex-6-ylmethyl]-(3-trifluoromethoxy-benzyl)-amide |
| 79 | 478.22 | 479.23 | 1-Methyl-1H-imidazole-4-carboxylic acid [3-(tetrahydro-furan-2-ylmethyl)-3-aza-bicyclo[3.1.0]hex-6-ylmethyl]-(3-trifluoromethoxy-benzyl)-amide |
| 80 | 474.2 | 475.4 | 1-Methyl-1H-imidazole-4-carboxylic acid [3-(1H-imidazol-2-ylmethyl)-3-aza-bicyclo[3.1.0]hex-6-ylmethyl]-(3-trifluoromethoxy-benzyl)-amide |
| 81 | 464.24 | 465.20 | 1-Methyl-1H-imidazole-4-carboxylic acid [3-(2-methyl-butyl)-3-aza-bicyclo[3.1.0]hex-6-ylmethyl]-(3-trifluoromethoxy-benzyl)-amide |
| 82 | 474.2 | 475.19 | 1-Methyl-1H-imidazole-4-carboxylic acid [3-(3H-imidazol-4-ylmethyl)-3-aza-bicyclo[3.1.0]hex-6-ylmethyl]-(3-trifluoromethoxy-benzyl)-amide |
| 83 | 464.24 | 465.20 | 1-Methyl-1H-imidazole-4-carboxylic acid [3-(3-methyl-butyl)-3-aza-bicyclo[3.1.0]hex-6-ylmethyl]-(3-trifluoromethoxy-benzyl)-amide |
| 84 | 478.26 | 479.26 | 1-Methyl-1H-imidazole-4-carboxylic acid [3-(2-ethyl-butyl)-3-aza-bicyclo[3.1.0]hex-6-ylmethyl]-(3-trifluoromethoxy-benzyl)-amide |
| 85 | 475.18 | 476.20 | 1-Methyl-1H-imidazole-4-carboxylic acid (3-isoxazol-3-ylmethyl-3-aza-bicyclo[3.1.0]hex-6-ylmethyl)-(3-trifluoromethoxy-benzyl)-amide |
| 86 | 478.26 | 479.28 | 1-Methyl-1H-imidazole-4-carboxylic acid [3-(2-methyl-pentyl)-3-aza-bicyclo[3.1.0]hex-6-ylmethyl]-(3-trifluoromethoxy-benzyl)-amide |
| 87 | 488.21 | 489.24 | 1-Methyl-1H-imidazole-4-carboxylic acid [3-(1-methyl-1H-pyrazol-4-ylmethyl)-3-aza-bicyclo[3.1.0]hex-6-ylmethyl]-(3-trifluoromethoxy-benzyl)-amide |
| 88 | 492.27 | 493.30 | 1-Methyl-1H-imidazole-4-carboxylic acid [3-(2-ethyl-3-methyl-butyl)-3-aza-bicyclo[3.1.0]hex-6-ylmethyl]-(3-trifluoromethoxy-benzyl)-amide |
| 89 | 490.26 | 491.28 | 1-Methyl-1H-imidazole-4-carboxylic acid (3-cyclohexylmethyl-3-aza-bicyclo[3.1.0]hex-6-ylmethyl)-(3-trifluoromethoxy-benzyl)-amide |
| 90 | 487.22 | 488.25 | 1-Methyl-1H-imidazole-4-carboxylic acid [3-(1-methyl-1H-pyrrol-2-ylmethyl)-3-aza-bicyclo[3.1.0]hex-6-ylmethyl]-(3-trifluoromethoxy-benzyl)-amide |
| 91 | 478.26 | 479.27 | 1-Methyl-1H-imidazole-4-carboxylic acid [3-(3,3-dimethyl-butyl)-3-aza-bicyclo[3.1.0]hex-6-ylmethyl]-(3-trifluoromethoxy-benzyl)-amide |
| 92 | 498.22 | 499.25 | 1-Methyl-1H-imidazole-4-carboxylic acid [3-(4-methyl-benzyl)-3-aza-bicyclo[3.1.0]hex-6-ylmethyl]-(3-trifluoromethoxy-benzyl)-amide |
| 93 | 492.27 | 493.30 | 1-Methyl-1H-imidazole-4-carboxylic acid (3-heptyl-3-aza-bicyclo[3.1.0]hex-6-ylmethyl)-(3-trifluoromethoxy-benzyl)-amide |
| 94 | 488.21 | 489.24 | 1-Methyl-1H-imidazole-4-carboxylic acid [3-(1-methyl-1H-imidazol-2-ylmethyl)-3-aza-bicyclol[3.1.0]hex-6-ylmethyl]-(3-trifluoromethoxy-benzyl)-amide |
| 95 | 498.22 | 499.24 | 1-Methyl-1H-imidazole-4-carboxylic acid [3-(2-methyl-benzyl)-3-aza-bicyclo[3.1.0]hex-6-ylmethyl]-(3-trifluoromethoxy-benzyl)-amide |
| 96 | 500.24 | 501.26 | 1-Methyl-1H-imidazole-4-carboxylic acid (3-bicyclo[2.2.1]hept-5-en-2-ylmethyl-3-aza-bicyclo[3.1.0]hex-6-ylmethyl)-(3-trifluoromethoxy-benzyl)-amide |
| 97 | 488.21 | 489.23 | 1-Methyl-1H-imidazole-4-carboxylic acid [3-(5-methyl-3H-imidazol-4-ylmethyl)-3-aza-bicyclo[3.1.0]hex-6-ylmethyl]-(3-trifluoromethoxy-benzyl)-amide |
| 98 | 512.24 | 513.24 | 1-Methyl-1H-imidazole-4-carboxylic acid [3-(2,4-dimethyl-benzyl)-3-aza-bicyclo[3.1.0]hex-6-ylmethyl]-(3-trifluoromethoxy-benzyl)-amide |
| 99 | 498.22 | 499.25 | 1-Methyl-1H-imidazole-4-carboxylic acid [3-(3-methyl-benzyl)-3-aza-bicyclo[3.1.0]hex-6-ylmethyl]-(3-trifluoromethoxy-benzyl)-amide |
| 100 | 502.23 | 503.25 | 1-Methyl-1H-imidazole-4-carboxylic acid [3-(1,5-dimethyl-1H-pyrazol-4-ylmethyl)-3-aza-bicyclo[3.1.0]hex-6-ylmethyl]-(3-trifluoromethoxy-benzyl)-amide |
| 101 | 509.2 | 510.21 | 1-Methyl-1H-imidazole-4-carboxylic acid [3-(4-cyano-benzyl)-3-aza-bicyclo[3.1.0]hex-6-ylmethyl]-(3-trifluoromethoxy-benzyl)-amide |
| 102 | 508.23 | 509.24 | 2-Methyl-3-(6-{[(1-methyl-1H-imidazole-4-carbonyl)-(3-trifluoromethoxy-benzyl)-amino]-methyl}-3-aza-bicyclo[3.1.0]hex-3-yl)-propionic acid ethyl ester |
| 103 | 498.22 | 499.24 | 1-Methyl-1H-imidazole-4-carboxylic acid (3-phenethyl-3-aza-bicyclo[3.1.0]hex-6-ylmethyl)-(3-trifluoromethoxy-benzyl)-amide |
| 104 | 502.23 | 503.25 | 1-Methyl-1H-imidazole-4-carboxylic acid [3-(2-ethyl-3H-imidazol-4-ylmethyl)-3-aza-bicyclo[3.1.0]hex-6-ylmethyl]-(3-trifluoromethoxy-benzyl)-amide |
| 105 | 512.24 | 513.25 | 1-Methyl-1H-imidazole-4-carboxylic acid [3-(4-ethyl-benzyl)-3-aza-bicyclo[3.1.0]hex-6-ylmethyl]-(3-trifluoromethoxy-benzyl)-amide |
| 106 | 501.2 | 502.21 | 1-Methyl-1H-imidazole-4-carboxylic acid [3-(6-oxo-1,6-dihydro-pyridin-2-ylmethyl)-3-aza-bicyclo[3.1.0]hex-6-ylmethyl]-(3-trifluoromethoxy-benzyl)-amide |
| 107 | 502.23 | 503.24 | 1-Methyl-1H-imidazole-4-carboxylic acid [3-(2,5-dimethyl-2H-pyrazol-3-ylmethyl)-3-aza-bicyclo[3.1.0]hex-6-ylmethyl]-(3-trifluoromethoxy-benzyl)-amide |
| 108 | 512.24 | 513.25 | 1-Methyl-1H-imidazole-4-carboxylic acid [3-(2-p-tolyl-ethyl)-3-aza-bicyclo[3.1.0]hex-6-ylmethyl]-(3-trifluoromethoxy-benzyl)-amide |
| 109 | 516.25 | 517.25 | 1-Methyl-1H-imidazole-4-carboxylic acid [3-(2-ethyl-5-methyl-3H-imidazol-4-ylmethyl)-3-aza-bicyclo[3.1.0]hex-6-ylmethyl]-(3-trifluoromethoxy-benzyl)-amide |
| 110 | 514.22 | 515.22 | 1-Methyl-1H-imidazole-4-carboxylic acid [3-(4-methoxy-benzyl)-3-aza-bicyclo[3.1.0]hex-6-ylmethyl]-(3-trifluoromethoxy-benzyl)-amide |
| 111 | 506.29 | 507.31 | 1-Methyl-1H-imidazole-4-carboxylic acid [3-(2-ethyl-hexyl)-3-aza-bicyclo[3.1.0]hex-6-ylmethyl]-(3-trifluoromethoxy-benzyl)-amide |
| 112 | 516.25 | 517.25 | 1-Methyl-1H-imidazole-4-carboxylic acid [3-(1-ethyl-3-methyl-1H-pyrazol-4-ylmethyl)-3-aza-bicyclo[3.1.0]hex-6-ylmethyl]-(3-trifluoromethoxy-benzyl)-amide |
| 113 | 518.21 | 519.21 | 1-Methyl-1H-imidazole-4-carboxylic acid [3-(5-methoxymethyl-furan-2-ylmethyl)-3- |

| Example | MW Calc | Mass Spec Data (M + 1) | IUPAC Name |
|---|---|---|---|
| 114 | 512.24 | 513.24 | aza-bicyclo[3.1.0]hex-6-ylmethyl]-(3-trifluoromethoxy-benzyl)-amide 1-Methyl-1H-imidazole-4-carboxylic acid [3-(3-phenyl-propyl)-3-aza-bicyclo[3.1.0]hex-6-ylmethyl]-(3-trifluoromethoxy-benzyl)-amide |
| 115 | 516.21 | 517.21 | 1-Methyl-1H-imidazole-4-carboxylic acid [3-(3-fluoro-4-methyl-benzyl)-3-aza-bicyclo[3.1.0]hex-6-ylmethyl]-(3-trifluoromethoxy-benzyl)-amide |
| 116 | 518.17 | 519.21 | 1-Methyl-1H-imidazole-4-carboxylic acid [3-(4-chloro-benzyl)-3-aza-bicyclo[3.1.0]hex-6-ylmethyl]-(3-trifluoromethoxy-benzyl)-amide |
| 117 | 516.25 | 517.26 | 1-Methyl-1H-imidazole-4-carboxylic acid [3-(1-ethyl-5-methyl-1H-pyrazol-4-ylmethyl)-3-aza-bicyclo[3.1.0]hex-6-ylmethyl]-(3-trifluoromethoxy-benzyl)-amide |
| 118 | 520.19 | 521.19 | 1-Methyl-1H-imidazole-4-carboxylic acid [3-(2,5-difluoro-benzyl)-3-aza-bicyclo[3.1.0]hex-6-ylmethyl]-(3-trifluoromethoxy-benzyl)-amide |
| 119 | 522.18 | 523.18 | 1-Methyl-1H-imidazole-4-carboxylic acid [3-(4-chloro-1-methyl-1H-pyrazol-3-ylmethyl)-3-aza-bicyclo[3.1.0]hex-6-ylmethyl]-(3-trifluoromethoxy-benzyl)-amide |
| 120 | 519.16 | 520.17 | 1-Methyl-1H-imidazole-4-carboxylic acid [3-(2-chloro-pyridin-3-ylmethyl)-3-aza-bicyclo[3.1.0]hex-6-ylmethyl]-(3-trifluoromethoxy-benzyl)-amide |
| 121 | 524.21 | 525.22 | 1-Methyl-1H-imidazole-4-carboxylic acid [3-(1H-benzoimidazol-2-ylmethyl)-3-aza-bicyclo[3.1.0]hex-6-ylmethyl]-(3-trifluoromethoxy-benzyl)-amide |
| 122 | 520.19 | 521.19 | 1-Methyl-1H-imidazole-4-carboxylic acid [3-(3,5-difluoro-benzyl)-3-aza-bicyclo[3.1.0]hex-6-ylmethyl]-(3-trifluoromethoxy-benzyl)-amide |
| 123 | 523.22 | 524.22 | 1-Methyl-1H-imidazole-4-carboxylic acid [3-(1H-indol-2-ylmethyl)-3-aza-bicyclo[3.1.0]hex-6-ylmethyl]-(3-trifluoromethoxy-benzyl)-amide |
| 124 | 525.12 | 526.13 | 1-Methyl-1H-imidazole-4-carboxylic acid [3-(2-chloro-thiazol-5-ylmethyl)-3-aza-bicyclo[3.1.0]hex-6-ylmethyl]-(3-trifluoromethoxy-benzyl)-amide |
| 125 | 520.19 | 521.19 | 1-Methyl-1H-imidazole-4-carboxylic acid [3-(2,3-difluoro-benzyl)-3-aza-bicyclo[3.1.0]hex-6-ylmethyl]-(3-trifluoromethoxy-benzyl)-amide |
| 126 | 523.22 | 524.22 | 1-Methyl-1H-imidazole-4-carboxylic acid [3-(1H-indol-5-ylmethyl)-3-aza-bicyclo[3.1.0]hex-6-ylmethyl]-(3-trifluoromethoxy-benzyl)-amide |
| 127 | 520.3 | 521.30 | 1-Methyl-1H-imidazole-4-carboxylic acid (3-trifluoromethoxy-benzyl)-[3-(3,5,5-trimethyl-hexyl)-3-aza-bicyclo[3.1.0]hex-6-ylmethyl]-amide |
| 128 | 520.19 | 521.20 | 1-Methyl-1H-imidazole-4-carboxylic acid [3-(2,4-difluoro-benzyl)-3-aza-bicyclo[3.1.0]hex-6-ylmethyl]-(3-trifluoromethoxy-benzyl)-amide |
| 129 | 526.26 | 527.25 | 1-Methyl-1H-imidazole-4-carboxylic acid [3-(4-isopropyl-benzyl)-3-aza-bicyclo[3.1.0]hex-6-ylmethyl]-(3-trifluoromethoxy-benzyl)-amide |
| 130 | 528.2 | 529.20 | 1-Methyl-1H-imidazole-4-carboxylic acid (3-benzo[1,3]dioxol-5-ylmethyl-3-aza-bicyclo[3.1.0]hex-6-ylmethyl)-(3-trifluoromethoxy-benzyl)-amide |
| 131 | 550.23 | 551.24 | 1-Methyl-1H-imidazole-4-carboxylic acid [3-(1-pyridin-2-yl-1H-pyrrol-2-ylmethyl)-3-aza-bicyclo[3.1.0]hex-6-ylmethyl]-(3-trifluoromethoxy-benzyl)-amide |
| 132 | 534.22 | 535.23 | 1-Methyl-1H-imidazole-4-carboxylic acid (3-naphthalen-2-ylmethyl-3-aza-bicyclo[3.1.0]hex-6-ylmethyl)-(3-trifluoromethoxy-benzyl)-amide |
| 133 | 528.2 | 529.20 | 1-Methyl-1H-imidazole-4-carboxylic acid (3-benzo[1,3]dioxol-4-ylmethyl-3-aza-bicyclo[3.1.0]hex-6-ylmethyl)-(3-trifluoromethoxy-benzyl)-amide |
| 134 | 551.23 | 552.24 | 1-Methyl-1H-imidazole-4-carboxylic acid [3-(1-pyrimidin-2-yl-1H-pyrrol-2-ylmethyl)-3-aza-bicyclo[3.1.0]hex-6-ylmethyl]-(3-trifluoromethoxy-benzyl)-amide |
| 135 | 534.22 | 535.23 | 1-Methyl-1H-imidazole-4-carboxylic acid (3-naphthalen-1-ylmethyl-3-aza-bicyclo[3.1.0]hex-6-ylmethyl)-(3-trifluoromethoxy-benzyl)-amide |
| 136 | 530.25 | 531.26 | 1-Methyl-1H-imidazole-4-carboxylic acid {3-[3-(5-methyl-furan-2-yl)-butyl]-3-aza-bicyclo[3.1.0]hex-6-ylmethyl}-(3-trifluoromethoxy-benzyl)-amide |
| 137 | 528.27 | 529.28 | 1-Methyl-1H-imidazole-4-carboxylic acid [3-(6,6-dimethyl-bicyclo[3.1.1]hept-2-en-2-ylmethyl)-3-aza-bicyclo[3.1.0]hex-6-ylmethyl]-(3-trifluoromethoxy-benzyl)-amide |
| 138 | 541.18 | 542.19 | 1-Methyl-1H-imidazole-4-carboxylic acid (3-benzothiazol-2-ylmethyl-3-aza-bicyclo[3.1.0]hex-6-ylmethyl)-(3-trifluoromethoxy-benzyl)-amide |
| 139 | 550.2 | 551.22 | 1-Methyl-1H-imidazole-4-carboxylic acid [3-(4-difluoromethoxy-benzyl)-3-aza-bicyclo[3.1.0]hex-6-ylmethyl]-(3-trifluoromethoxy-benzyl)-amide |
| 140 | 552.2 | 553.22 | 1-Methyl-1H-imidazole-4-carboxylic acid (3-trifluoromethoxy-benzyl)-[3-(4-trifluoromethyl-benzyl)-3-aza-bicyclo[3.1.0]hex-6-ylmethyl]-amide |
| 141 | 560.24 | 561.26 | 1-Methyl-1H-imidazole-4-carboxylic acid (3-biphenyl-4-ylmethyl-3-aza-bicyclo[3.1.0]hex-6-ylmethyl)-(3-trifluoromethoxy-benzyl)-amide |
| 142 | 568.19 | 569.22 | 1-Methyl-1H-imidazole-4-carboxylic acid (3-trifluoromethoxy-benzyl)-[3-(3-trifluoromethoxy-benzyl)-3-aza-bicyclo[3.1.0]hex-6-ylmethyl]-amide |
| 143 | 526.26 | 527.26 | 1-Methyl-1H-imidazole-4-carboxylic acid [3-(3-phenyl-butyl)-3-aza-bicyclo[3.1.0]hex-6-ylmethyl]-(3-trifluoromethoxy-benzyl)-amide |
| 144 | 577.23 | 578.22 | 1-Methyl-1H-imidazole-4-carboxylic acid [3-(6-phenoxy-pyridin-3-ylmethyl)-3-aza-bicyclo[3.1.0]hex-6-ylmethyl]-(3-trifluoromethoxy-benzyl)-amide |
| 145 | 576.23 | 577.23 | 1-Methyl-1H-imidazole-4-carboxylic acid [3-(4-phenoxy-benzyl)-3-aza-bicyclo[3.1.0]hex-6-ylmethyl]-(3-trifluoromethoxy-benzyl)-amide |
| 146 | 568.19 | 569.21 | 1-Methyl-1H-imidazole-4-carboxylic acid (3-trifluoromethoxy-benzyl)-[3-(2-trifluoromethoxy-benzyl)-3-aza-bicyclo[3.1.0]hex-6-ylmethyl]-amide |
| 147 | 502.2 | 503.24 | 1-Methyl-1H-imidazole-4-carboxylic acid [3-(4-fluoro-benzyl)-3-aza-bicyclo[3.1.0]hex-6-ylmethyl]-(3-trifluoromethoxy-benzyl)-amide |
| 148 | 450.2 | 451.2 | 1-Methyl-1H-imidazole-4-carboxylic acid (3-cyclopropylmethyl-3-aza-bicyclo[3.1.0]hex-6-ylmethyl)-(4-fluoro-3-trifluoromethyl-benzyl)-amide |
| 149 | 478.24 | 479.2 | 1-Methyl-1H-imidazole-4-carboxylic acid (3-cyclopentylmethyl-3-aza-bicyclo[3.1.0]hex-6-ylmethyl)-(4-fluoro-3-trifluoromethyl-benzyl)-amide |

| Example | MW Calc | Mass Spec Data (M + 1) | IUPAC Name |
|---|---|---|---|
| 150 | 570.19 | 571.2 | 1-Methyl-1H-imidazole-4-carboxylic acid (4-fluoro-3-trifluoromethyl-benzyl)-[3-(4-trifluoromethoxy-benzyl)-3-aza-bicyclo[3.1.0]hex-6-ylmethyl]-amide |
| 151 | 508.25 | 509.2 | 1-Methyl-1H-imidazole-4-carboxylic acid (4-fluoro-3-trifluoromethyl-benzyl)-[3-(1-hydroxy-cyclohexylmethyl)-3-aza-bicyclo[3.1.0]hex-6-ylmethyl]-amide |
| 152 | 578.23 | 579.2 | 1-Methyl-1H-imidazole-4-carboxylic acid (4-fluoro-3-trifluoromethyl-benzyl)-[3-(4-phenoxy-benzyl)-3-aza-bicyclo[3.1.0]hex-6-ylmethyl]-amide |
| 153 | 501.17 | 502.3 | Thiazole-4-carboxylic acid (3-phenethyl-3-aza-bicyclo[3.1.0]hex-6-ylmethyl)-(3-trifluoromethoxy-benzyl)-amide |
| 154 | 451.15 | 452.3 | Thiazole-4-carboxylic acid (3-cyclopropylmethyl-3-aza-bicyclo[3.1.0]hex-6-ylmethyl)-(3-trifluoromethoxy-benzyl)-amide |
| 155 | 479.19 | 480.3 | Thiazole-4-carboxylic acid (3-cyclopentylmethyl-3-aza-bicyclo[3.1.0]hex-6-ylmethyl)-(3-trifluoromethoxy-benzyl)-amide |
| 156 | 521.12 | 521.89 | Thiazole-4-carboxylic acid [3-(4-chloro-benzyl)-3-aza-bicyclo[3.1.0]hex-6-ylmethyl]-(3-trifluoromethoxy-benzyl)-amide |
| 157 | 505.14 | 506.3 | Thiazole-4-carboxylic acid [3-(4-fluoro-benzyl)-3-aza-bicyclo[3.1.0]hex-6-ylmethyl]-(3-trifluoromethoxy-benzyl)-amide |
| 158 | 523.24 | 524.4 | 1-Methyl-1H-imidazole-4-carboxylic acid (3-{[ethyl-(2-hydroxy-ethyl)-carbamoyl]-methyl}-3-aza-bicyclo[3.1.0]hex-6-ylmethyl)-(3-trifluoromethoxy-benzyl)-amide |
| 159 | 521.26 | 522.4 | 1-Methyl-1H-imidazole-4-carboxylic acid {3-[(sec-butyl-methyl-carbamoyl)-methyl]-3-aza-bicyclo[3.1.0]hex-6-ylmethyl}-(3-trifluoromethoxy-benzyl)-amide |
| 160 | 531.22 | 531.8 | 1-Methyl-1H-imidazole-4-carboxylic acid {3-[(1-methyl-1H-pyrazol-3-ylcarbamoyl)-methyl]-3-aza-bicyclo[3.1.0]hex-6-ylmethyl}-(3-trifluoromethoxy-benzyl)-amide |
| 161 | 491.21 | 492.4 | 1-Methyl-1H-imidazole-4-carboxylic acid (3-cyclopropylcarbamoylmethyl-3-aza-bicyclo[3.1.0]hex-6-ylmethyl)-(3-trifluoromethoxy-benzyl)-amide |
| 162 | 434.19 | 435.1 | 1H-Imidazole-4-carboxylic acid (3-cyclopropylmethyl-3-aza-bicyclo[3.1.0]hex-6-ylmethyl)-(3-trifluoromethoxy-benzyl)-amide |
| 163 | 380.15 | 381.1 | 1H-Imidazole-4-carboxylic acid (3-aza-bicyclo[3.1.0]hex-6-ylmethyl)-(3-trifluoromethoxy-benzyl)-amide |
| 164 | 505.23 | 506.41 | 1-Methyl-1H-imidazole-4-carboxylic acid {3-[(cyclopropylmethyl-carbamoyl)-methyl]-3-aza-bicyclo[3.1.0]hex-6-ylmethyl}-(3-trifluoromethoxy-benzyl)-amide |
| 165 | 507.25 | 508.42 | 1-Methyl-1H-imidazole-4-carboxylic acid [3-(tert-butylcarbamoyl-methyl)-3-aza-bicyclo[3.1.0]hex-6-ylmethyl]-(3-trifluoromethoxy-benzyl)-amide |
| 166 | 505.23 | 506.41 | 1-Methyl-1H-imidazole-4-carboxylic acid (3-cyclobutylcarbamoylmethyl-3-aza-bicyclo[3.1.0]hex-6-ylmethyl)-(3-trifluoromethoxy-benzyl)-amide |
| 167 | 509.22 | 510.4 | 1-Methyl-1H-imidazole-4-carboxylic acid {3-[(2-methoxy-ethylcarbamoyl)-methyl]-3-aza-bicyclo[3.1.0]hex-6-ylmethyl}-(3-trifluoromethoxy-benzyl)-amide |
| 168 | 523.24 | 524.42 | 1-Methyl-1H-imidazole-4-carboxylic acid {3-[(2-methoxy-1-methyl-ethylcarbamoyl)-methyl]-3-aza-bicyclo[3.1.0]hex-6-ylmethyl}-(3-trifluoromethoxy-benzyl)-amide |
| 169 | 519.25 | 520.42 | 1-Methyl-1H-imidazole-4-carboxylic acid (3-cyclopentylcarbamoylmethyl-3-aza-bicyclo[3.1.0]hex-6-ylmethyl)-(3-trifluoromethoxy-benzyl)-amide |
| 170 | 509.22 | 510.4 | 1-Methyl-1H-imidazole-4-carboxylic acid {3-[(2-hydroxy-propylcarbamoyl)-methyl]-3-aza-bicyclo[3.1.0]hex-6-ylmethyl}-(3-trifluoromethoxy-benzyl)-amide |
| 171 | 527.21 | 528.38 | 1-Methyl-1H-imidazole-4-carboxylic acid (3-phenylcarbamoylmethyl-3-aza-bicyclo[3.1.0]hex-6-ylmethyl)-(3-trifluoromethoxy-benzyl)-amide |
| 172 | 517.2 | 518.38 | 1-Methyl-1H-imidazole-4-carboxylic acid {3-[(1H-imidazol-2-ylcarbamoyl)-methyl]-3-aza-bicyclo[3.1.0]hex-6-ylmethyl}-(3-trifluoromethoxy-benzyl)-amide |
| 173 | 493.23 | 494.41 | 1-Methyl-1H-imidazole-4-carboxylic acid [3-(isopropylcarbamoyl-methyl)-3-aza-bicyclo[3.1.0]hex-6-ylmethyl]-(3-trifluoromethoxy-benzyl)-amide |
| 174 | 521.26 | 522.44 | 1-Methyl-1H-imidazole-4-carboxylic acid {3-[(2,2-dimethyl-propylcarbamoyl)-methyl]-3-aza-bicyclo[3.1.0]hex-6-ylmethyl}-(3-trifluoromethoxy-benzyl)-amide |
| 175 | 528.21 | 529.38 | 1-Methyl-1H-imidazole-4-carboxylic acid [3-(pyridin-3-ylcarbamoylmethyl)-3-aza-bicyclo[3.1.0]hex-6-ylmethyl]-(3-trifluoromethoxy-benzyl)-amide |
| 176 | 570.26 | 571.42 | 1-Methyl-1H-imidazole-4-carboxylic acid (3-{[methyl-(3-methyl-pyridin-2-ylmethyl)-carbamoyl]-methyl}-3-aza-bicyclo[3.1.0]hex-6-ylmethyl)-(3-trifluoromethoxy-benzyl)-amide |
| 177 | 523.24 | 524.42 | 1-Methyl-1H-imidazole-4-carboxylic acid {3-[(2-hydroxy-1,1-dimethyl-ethylcarbamoyl)-methyl]-3-aza-bicyclo[3.1.0]hex-6-ylmethyl}-(3-trifluoromethoxy-benzyl)-amide |
| 178 | 528.21 | 529.38 | 1-Methyl-1H-imidazole-4-carboxylic acid [3-(pyridin-2-ylcarbamoylmethyl)-3-aza-bicyclo[3.1.0]hex-6-ylmethyl]-(3-trifluoromethoxy-benzyl)-amide |
| 179 | 531.22 | 532.39 | 1-Methyl-1H-imidazole-4-carboxylic acid {3-[(2-methyl-2H-pyrazol-3-ylcarbamoyl)-methyl]-3-aza-bicyclo[3.1.0]hex-6-ylmethyl}-(3-trifluoromethoxy-benzyl)-amide |
| 180 | 533.19 | 534.36 | 1-Methyl-1H-imidazole-4-carboxylic acid {3-[(2,2,2-trifluoro-ethylcarbamoyl)-methyl]-3-aza-bicyclo[3.1.0]hex-6-ylmethyl}-(3-trifluoromethoxy-benzyl)-amide |
| 181 | 531.21 | 532.38 | 1-Methyl-1H-imidazole-4-carboxylic acid (3-{[(furan-2-ylmethyl)-carbamoyl]-methyl}-3-aza-bicyclo[3.1.0]hex-6-ylmethyl)-(3-trifluoromethoxy-benzyl)-amide |
| 182 | 479.21 | 480.4 | 1-Methyl-1H-imidazole-4-carboxylic acid (3-dimethylcarbamoylmethyl-3-aza-bicyclo[3.1.0]hex-6-ylmethyl)-(3-trifluoromethoxy-benzyl)-amide |
| 183 | 532.22 | 533.39 | 1-Methyl-1H-imidazole-4-carboxylic acid {3-[(1-methyl-1H-[1,2,4]triazol-3-ylcarbamoyl)-methyl]-3-aza-bicyclo[3.1.0]hex-6-ylmethyl}-(3-trifluoromethoxy-benzyl)-amide |
| 184 | 533.26 | 534.44 | 1-Methyl-1H-imidazole-4-carboxylic acid (3-cyclohexylcarbamoylmethyl-3-aza-bicyclo[3.1.0]hex-6-ylmethyl)-(3-trifluoromethoxy-benzyl)-amide |
| 185 | 505.23 | 506.41 | 1-Methyl-1H-imidazole-4-carboxylic acid [3-(2-oxo-2-pyrrolidin-1-yl-ethyl)-3-aza- |

| Example | MW Calc | Mass Spec Data (M + 1) | IUPAC Name |
|---|---|---|---|
| 186 | 519.25 | 520.42 | bicyclo[3.1.0]hex-6-ylmethyl)-(3-trifluoromethoxy-benzyl)-amide<br>1-Methyl-1H-imidazole-4-carboxylic acid {3-[2-(2-methyl-pyrrolidin-1-yl)-2-oxo-ethyl]-3-aza-bicyclo[3.1.0]hex-6-ylmethyl}-(3-trifluoromethoxy-benzyl)-amide |
| 187 | 519.25 | 520.43 | 1-Methyl-1H-imidazole-4-carboxylic acid [3-2-oxo-2-piperidin-1-yl-ethyl)-3-aza-bicyclo[3.1.0]hex-6-ylmethyl]-(3-trifluoromethoxy-benzyl)-amide |
| 188 | 519.25 | 520.42 | 1-Methyl-1H-imidazole-4-carboxylic acid {3-[(cyclopropylmethyl-methyl-carbamoyl)-methyl]-3-aza-bicyclo[3.1.0]hex-6-ylmethyl}-(3-trifluoromethoxy-benzyl)-amide |
| 189 | 521.22 | 522.4 | 1-Methyl-1H-imidazole-4-carboxylic acid [3-(2-morpholin-4-yl-2-oxo-ethyl)-3-aza-bicyclo[3.1.0]hex-6-ylmethyl]-(3-trifluoromethoxy-benzyl)-amide |
| 190 | 521.22 | 522.4 | 1-Methyl-1H-imidazole-4-carboxylic acid {3-[2-(3-hydroxy-pyrrolidin-1-yl)-2-oxo-ethyl]-3-aza-bicyclo[3.1.0]hex-6-ylmethyl}-(3-trifluoromethoxy-benzyl)-amide |
| 191 | 521.22 | 522.4 | 1-Methyl-1H-imidazole-4-carboxylic acid {3-[2-(3-hydroxy-pyrrolidin-1-yl)-2-oxo-ethyl]-3-aza-bicyclo[3.1.0]hex-6-ylmethyl}-(3-trifluoromethoxy-benzyl)-amide |
| 192 | 521.22 | 522.4 | 1-Methyl-1H-imidazole-4-carboxylic acid {3-[2-(3-hydroxy-pyrrolidin-1-yl)-2-oxo-ethyl]-3-aza-bicyclo[3.1.0]hex-6-ylmethyl}-(3-trifluoromethoxy-benzyl)-amide |
| 193 | 521.26 | 522.44 | 1-Methyl-1H-imidazole-4-carboxylic acid {3-[(ethyl-isopropyl-carbamoyl)-methyl]-3-aza-bicyclo[3.1.0]hex-6-ylmethyl}-(3-trifluoromethoxy-benzyl)-amide |
| 194 | 522.22 | 523.4 | 1-Methyl-1H-imidazole-4-carboxylic acid {3-[(carbamoylmethyl-methyl-carbamoyl)-methyl]-3-aza-bicyclo[3.1.0]hex-6-ylmethyl}-(3-trifluoromethoxy-benzyl)-amide |
| 195 | 533.26 | 534.44 | 1-Methyl-1H-imidazole-4-carboxylic acid {3-[2-(3-methyl-piperidin-1-yl)-2-oxo-ethyl]-3-aza-bicyclo[3.1.0]hex-6-ylmethyl}-(3-trifluoromethoxy-benzyl)-amide |
| 196 | 533.26 | 534.44 | 1-Methyl-1H-imidazole-4-carboxylic acid {3-[2-(4-methyl-piperidin-1-yl)-2-oxo-ethyl]-3-aza-bicyclo[3.1.0]hex-6-ylmethyl}-(3-trifluoromethoxy-benzyl)-amide |
| 197 | 523.19 | 524.36 | 1-Methyl-1H-imidazole-4-carboxylic acid [3-(2-oxo-2-thiazolidin-3-yl-ethyl)-3-aza-bicyclo[3.1.0]hex-6-ylmethyl]-(3-trifluoromethoxy-benzyl)-amide |
| 198 | 535.24 | 536.41 | 1-Methyl-1H-imidazole-4-carboxylic acid {3-[2-(3-hydroxymethyl-pyrrolidin-1-yl)-2-oxo-ethyl]-3-aza-bicyclo[3.1.0]hex-6-ylmethyl}-(3-trifluoromethoxy-benzyl)-amide |
| 199 | 535.24 | 536.42 | 1-Methyl-1H-imidazole-4-carboxylic acid {3-[2-(2-hydroxymethyl-pyrrolidin-1-yl)-2-oxo-ethyl]-3-aza-bicyclo[3.1.0]hex-6-ylmethyl}-(3-trifluoromethoxy-benzyl)-amide |
| 200 | 535.24 | 536.41 | 1-Methyl-1H-imidazole-4-carboxylic acid {3-[2-(3-hydroxy-piperidin-1-yl)-2-oxo-ethyl]-3-aza-bicyclo[3.1.0]hex-6-ylmethyl}-(3-trifluoromethoxy-benzyl)-amide |
| 201 | 537.2 | 537.91 | 1-Methyl-1H-imidazole-4-carboxylic acid [3-(2-oxo-2-thiomorpholin-4-yl-ethyl)-3-aza-bicyclo[3.1.0]hex-6-ylmethyl]-(3-trifluoromethoxy-benzyl)-amide |
| 202 | 549.26 | 549.98 | 1-Methyl-1H-imidazole-4-carboxylic acid {3-[2-(2,6-dimethyl-morpholin-4-yl)-2-oxo-ethyl]-3-aza-bicyclo[3.1.0]hex-6-ylmethyl}-(3-trifluoromethoxy-benzyl)-amide |
| 203 | 561.2 | 561.9 | 1-Methyl-1H-imidazole-4-carboxylic acid {3-[(methyl-thiophen-2-ylmethyl-carbamoyl)-methyl]-3-aza-bicyclo[3.1.0]hex-6-ylmethyl}-(3-trifluoromethoxy-benzyl)-amide |
| 204 | 545.22 | 545.94 | 1-Methyl-1H-imidazole-4-carboxylic acid {3-[(furan-2-ylmethyl-methyl-carbamoyl)-methyl]-3-aza-bicyclo[3.1.0]hex-6-ylmethyl}-(3-trifluoromethoxy-benzyl)-amide |
| 205 | 555.25 | 555.98 | 1-Methyl-1H-imidazole-4-carboxylic acid {3-[(benzyl-methyl-carbamoyl)-methyl]-3-aza-bicyclo[3.1.0]hex-6-ylmethyl}-(3-trifluoromethoxy-benzyl)-amide |
| 206 | 553.23 | 553.93 | 1-Methyl-1H-imidazole-4-carboxylic acid {3-[2-(1,3-dihydro-isoindol-2-yl)-2-oxo-ethyl]-3-aza-bicyclo[3.1.0]hex-6-ylmethyl}-(3-trifluoromethoxy-benzyl)-amide |
| 207 | 541.21 | 541.91 | 1-Methyl-1H-imidazole-4-carboxylic acid {3-[2-(3,4-difluoro-pyrrolidin-1-yl)-2-oxo-ethyl]-3-aza-bicyclo[3.1.0]hex-6-ylmethyl}-(3-trifluoromethoxy-benzyl)-amide |
| 208 | 547.2 | 547.89 | 1-Methyl-1H-imidazole-4-carboxylic acid (3-{[methyl-(2,2,2-trifluoro-ethyl)-carbamoyl]-methyl}-3-aza-bicyclo[3.1.0]hex-6-ylmethyl)-(3-trifluoromethoxy-benzyl)-amide |
| 209 | 561.2 | 561.91 | 1-Methyl-1H-imidazole-4-carboxylic acid {3-[(methyl-thiophen-3-ylmethyl-carbamoyl)-methyl]-3-aza-bicyclo[3.1.0]hex-6-ylmethyl}-(3-trifluoromethoxy-benzyl)-amide |
| 210 | 569.26 | 569.99 | 1-Methyl-1H-imidazole-4-carboxylic acid {3-[(methyl-phenethyl-carbamoyl)-methyl]-3-aza-bicyclo[3.1.0]hex-6-ylmethyl}-(3-trifluoromethoxy-benzyl)-amide |
| 211 | 570.26 | 570.95 | 1-Methyl-1H-imidazole-4-carboxylic acid (3-{[methyl-(1-pyridin-4-yl-ethyl)-carbamoyl]-methyl}-3-aza-bicyclo[3.1.0]hex-6-ylmethyl)-(3-trifluoromethoxy-benzyl)-amide |
| 212 | 581.26 | 582.01 | 1-Methyl-1H-imidazole-4-carboxylic acid {3-[2-oxo-2-(3-phenyl-pyrrolidin-1-yl)-ethyl]-3-aza-bicyclo[3.1.0]hex-6-ylmethyl}-(3-trifluoromethoxy-benzyl)-amide |
| 213 | 571.21 | 571.92 | 1-Methyl-1H-imidazole-4-carboxylic acid (3-{[(2-methanesulfonyl-ethyl)-methyl-carbamoyl]-methyl}-3-aza-bicyclo[3.1.0]hex-6-ylmethyl)-(3-trifluoromethoxy-benzyl)-amide |
| 214 | 582.26 | 582.99 | 1-Methyl-1H-imidazole-4-carboxylic acid {3-[2-oxo-2-(2-pyridin-4-yl-pyrrolidin-1-yl)-ethyl]-3-aza-bicyclo[3.1.0]hex-6-ylmethyl}-(3-trifluoromethoxy-benzyl)-amide |
| 215 | 542.23 | 543.2 | 1-Methyl-1H-imidazole-4-carboxylic acid (4-fluoro-3-trifluoromethyl-benzyl)-[3-(2-hydroxy-indan-2-ylmethyl)-3-aza-bicyclo[3.1.0]hex-6-ylmethyl]-amide |
| 216 | 579.23 | 580.2 | 1-Methyl-1H-imidazole-4-carboxylic acid (4-fluoro-3-trifluoromethyl-benzyl)-[3-(6-phenoxy-pyridin-3-ylmethyl)-3-aza-bicyclo[3.1.0]hex-6-ylmethyl]-amide |
| 217 | 501.17 | 502.12 | Thiazole-4-carboxylic acid [3-(3-methyl-benzyl)-3-aza-bicyclo[3.1.0]hex-6-ylmethyl]-(3-trifluoromethoxy-benzyl)-amide |
| 218 | 505.14 | 505.91 | Thiazole-4-carboxylic acid [3-(2-fluoro-benzyl)-3-aza-bicyclo[3.1.0]hex-6-ylmethyl]-(3-trifluoromethoxy-benzyl)-amide |
| 219 | 517.16 | 518.16 | Thiazole-4-carboxylic acid [3-(4-methoxy-benzyl)-3-aza-bicyclo[3.1.0]hex-6-ylmethyl]-(3-trifluoromethoxy-benzyl)-amide |
| 220 | 493.2 | 494.10 | Thiazole-4-carboxylic acid (3-cyclohexylmethyl-3-aza-bicyclo[3.1.0]hex-6-ylmethyl)-(3-trifluoromethoxy-benzyl)-amide |

| Example | MW Calc | Mass Spec Data (M + 1) | IUPAC Name |
|---|---|---|---|
| 221 | 505.14 | 506.05 | Thiazole-4-carboxylic acid [3-(3-fluoro-benzyl)-3-aza-bicyclo[3.1.0]hex-6-ylmethyl]-(3-trifluoromethoxy-benzyl)-amide |
| 222 | 501.17 | 502.07 | Thiazole-4-carboxylic acid [3-(2-methyl-benzyl)-3-aza-bicyclo[3.1.0]hex-6-ylmethyl]-(3-trifluoromethoxy-benzyl)-amide |
| 223 | 579.18 | 580.07 | Thiazole-4-carboxylic acid [3-(4-phenoxy-benzyl)-3-aza-bicyclo[3.1.0]hex-6-ylmethyl]-(3-trifluoromethoxy-benzyl)-amide |
| 224 | 515.19 | 515.97 | Thiazole-4-carboxylic acid [3-(2-phenyl-propyl)-3-aza-bicyclo[3.1.0]hex-6-ylmethyl]-(3-trifluoromethoxy-benzyl)-amide |
| 225 | 512.15 | 512.93 | Thiazole-4-carboxylic acid [3-(4-cyano-benzyl)-3-aza-bicyclo[3.1.0]hex-6-ylmethyl]-(3-trifluoromethoxy-benzyl)-amide |
| 226 | 563.19 | 563.99 | Thiazole-4-carboxylic acid (3-biphenyl-4-ylmethyl-3-aza-bicyclo[3.1.0]hex-6-ylmethyl)-(3-trifluoromethoxy-benzyl)-amide |
| 227 | 512.15 | 512.84 | Thiazole-4-carboxylic acid [3-(3-cyano-benzyl)-3-aza-bicyclo[3.1.0]hex-6-ylmethyl]-(3-trifluoromethoxy-benzyl)-amide |
| 228 | 555.14 | 556.03 | Thiazole-4-carboxylic acid (3-trifluoromethoxy-benzyl)-[3-(4-trifluoromethyl-benzyl)-3-aza-bicyclo[3.1.0]hex-6-ylmethyl]-amide |
| 229 | 515.19 | 516.08 | Thiazole-4-carboxylic acid [3-(3,5-dimethyl-benzyl)-3-aza-bicyclo[3.1.0]hex-6-ylmethyl]-(3-trifluoromethoxy-benzyl)-amide |
| 230 | 521.12 | 521.91 | Thiazole-4-carboxylic acid [3-(3-chloro-benzyl)-3-aza-bicyclo[3.1.0]hex-6-ylmethyl]-(3-trifluoromethoxy-benzyl)-amide |
| 231 | 515.19 | 516.10 | Thiazole-4-carboxylic acid [3-(2,4-dimethyl-benzyl)-3-aza-bicyclo[3.1.0]hex-6-ylmethyl]-(3-trifluoromethoxy-benzyl)-amide |
| 232 | 571.14 | 572.00 | Thiazole-4-carboxylic acid (3-trifluoromethoxy-benzyl)-[3-(3-trifluoromethoxy-benzyl)-3-aza-bicyclo[3.1.0]hex-6-ylmethyl]-amide |
| 233 | 515.19 | 516.08 | Thiazole-4-carboxylic acid [3-(4-ethyl-benzyl)-3-aza-bicyclo[3.1.0]hex-6-ylmethyl]-(3-trifluoromethoxy-benzyl)-amide |
| 234 | 571.14 | 572.04 | Thiazole-4-carboxylic acid (3-trifluoromethoxy-benzyl)-[3-(4-trifluoromethoxy-benzyl)-3-aza-bicyclo[3.1.0]hex-6-ylmethyl]-amide |
| 235 | 491.16 | 491.99 | Thiazole-4-carboxylic acid [3-(1-methyl-1H-imidazol-2-ylmethyl)-3-aza-bicyclo[3.1.0]hex-6-ylmethyl]-(3-trifluoromethoxy-benzyl)-amide |
| 236 | 521.16 | 522.18 | Thiazole-4-carboxylic acid [3-(5-methoxymethyl-furan-2-ylmethyl)-3-aza-bicyclo[3.1.0]hex-6-ylmethyl]-(3-trifluoromethoxy-benzyl)-amide |
| 237 | 504.14 | 504.91 | Thiazole-4-carboxylic acid [3-(6-oxo-1,6-dihydro-pyridin-2-ylmethyl)-3-aza-bicyclo[3.1.0]hex-6-ylmethyl]-(3-trifluoromethoxy-benzyl)-amide |
| 238 | 519.19 | 519.99 | Thiazole-4-carboxylic acid [3-(1-ethyl-3-methyl-1H-pyrazol-4-ylmethyl)-3-aza-bicyclo[3.1.0]hex-6-ylmethyl]-(3-trifluoromethoxy-benzyl)-amide |
| 239 | 490.17 | 490.97 | Thiazole-4-carboxylic acid [3-(1-methyl-1H-pyrrol-2-ylmethyl)-3-aza-bicyclo[3.1.0]hex-6-ylmethyl]-(3-trifluoromethoxy-benzyl)-amide |
| 240 | 571.14 | 571.76 | Thiazole-4-carboxylic acid (3-trifluoromethoxy-benzyl)-[3-(2-trifluoromethoxy-benzyl)-3-aza-bicyclo[3.1.0]hex-6-ylmethyl]-amide |
| 241 | 477.13 | 477.98 | Thiazole-4-carboxylic acid (3-furan-3-ylmethyl-3-aza-bicyclo[3.1.0]hex-6-ylmethyl)-(3-trifluoromethoxy-benzyl)-amide |
| 242 | 505.18 | 506.06 | Thiazole-4-carboxylic acid [3-(1,5-dimethyl-1H-pyrazol-4-ylmethyl)-3-aza-bicyclo[3.1.0]hex-6-ylmethyl]-(3-trifluoromethoxy-benzyl)-amide |
| 243 | 477.14 | 477.85 | Thiazole-4-carboxylic acid [3-(1H-imidazol-4-ylmethyl)-3-aza-bicyclo[3.1.0]hex-6-ylmethyl]-(3-trifluoromethoxy-benzyl)-amide |
| 244 | 476.15 | 476.95 | Thiazole-4-carboxylic acid [3-(1H-pyrrol-2-ylmethyl)-3-aza-bicyclo[3.1.0]hex-6-ylmethyl]-(3-trifluoromethoxy-benzyl)-amide |
| 245 | 515.19 | 516.10 | Thiazole-4-carboxylic acid [3-(3-phenyl-propyl)-3-aza-bicyclo[3.1.0]hex-6-ylmethyl]-(3-trifluoromethoxy-benzyl)-amide |
| 246 | 491.16 | 492.00 | Thiazole-4-carboxylic acid [3-(1-methyl-1H-pyrazol-4-ylmethyl)-3-aza-bicyclo[3.1.0]hex-6-ylmethyl]-(3-trifluoromethoxy-benzyl)-amide |
| 247 | 519.16 | 520.18 | Thiazole-4-carboxylic acid [3-(4-fluoro-3-methyl-benzyl)-3-aza-bicyclo[3.1.0]hex-6-ylmethyl]-(3-trifluoromethoxy-benzyl)-amide |
| 248 | 491.16 | 491.84 | Thiazole-4-carboxylic acid [3-(5-methyl-3H-imidazol-4-ylmethyl)-3-aza-bicyclo[3.1.0]hex-6-ylmethyl]-(3-trifluoromethoxy-benzyl)-amide |
| 249 | 477.13 | 477.90 | Thiazole-4-carboxylic acid (3-furan-2-ylmethyl-3-aza-bicyclo[3.1.0]hex-6-ylmethyl)-(3-trifluoromethoxy-benzyl)-amide |
| 250 | 511.18 | 512.14 | (6-{[(Thiazole-4-carbonyl)-(3-trifluoromethoxy-benzyl)-amino]-methyl}-3-aza-bicyclo[3.1.0]hex-3-yl)-acetic acid butyl ester |
| 251 | 519.16 | 520.08 | Thiazole-4-carboxylic acid [3-(3-fluoro-4-methyl-benzyl)-3-aza-bicyclo[3.1.0]hex-6-ylmethyl]-(3-trifluoromethoxy-benzyl)-amide |
| 252 | 505.18 | 505.96 | Thiazole-4-carboxylic acid [3-(2-ethyl-3H-imidazol-4-ylmethyl)-3-aza-bicyclo[3.1.0]hex-6-ylmethyl]-(3-trifluoromethoxy-benzyl)-amide |
| 253 | 519.19 | 520.03 | Thiazole-4-carboxylic acid [3-(2-ethyl-5-methyl-3H-imidazol-4-ylmethyl)-3-aza-bicyclo[3.1.0]hex-6-ylmethyl]-(3-trifluoromethoxy-benzyl)-amide |
| 254 | 481.16 | 482.02 | Thiazole-4-carboxylic acid [3-(tetrahydro-furan-2-ylmethyl)-3-aza-bicyclo[3.1.0]hex-6-ylmethyl]-(3-trifluoromethoxy-benzyl)-amide |
| 255 | 515.19 | 516.08 | Thiazole-4-carboxylic acid [3-(2-p-tolyl-ethyl)-3-aza-bicyclo[3.1.0]hex-6-ylmethyl]-(3-trifluoromethoxy-benzyl)-amide |
| 256 | 519.19 | 520.08 | Thiazole-4-carboxylic acid [3-(1-ethyl-5-methyl-1H-pyrazol-4-ylmethyl)-3-aza-bicyclo[3.1.0]hex-6-ylmethyl]-(3-trifluoromethoxy-benzyl)-amide |
| 257 | 522.11 | 522.87 | Thiazole-4-carboxylic acid [3-(2-chloro-pyridin-3-ylmethyl)-3-aza-bicyclo[3.1.0]hex-6-ylmethyl]-(3-trifluoromethoxy-benzyl)-amide |
| 258 | 478.13 | 479.04 | Thiazole-4-carboxylic acid (3-isoxazol-3-ylmethyl-3-aza-bicyclo[3.1.0]hex-6-ylmethyl)-(3-trifluoromethoxy-benzyl)-amide |

| Example | MW Calc | Mass Spec Data (M + 1) | IUPAC Name |
|---|---|---|---|
| 259 | 526.17 | 527.01 | Thiazole-4-carboxylic acid [3-(1H-indol-3-ylmethyl)-3-aza-bicyclo[3.1.0]hex-6-ylmethyl]-(3-trifluoromethoxy-benzyl)-amide |
| 260 | 511.18 | 511.90 | 2-Methyl-3-(6-{[(thiazole-4-carbonyl)-(3-trifluoromethoxy-benzyl)-amino]-methyl}-3-aza-bicyclo[3.1.0]hex-3-yl)-propionic acid ethyl ester |
| 261 | 491.16 | 492.00 | Thiazole-4-carboxylic acid [3-(5-methyl-2H-pyrazol-3-ylmethyl)-3-aza-bicyclo[3.1.0]hex-6-ylmethyl]-(3-trifluoromethoxy-benzyl)-amide |
| 262 | 559.21 | 560.09 | Thiazole-4-carboxylic acid [3-(4-butoxy-benzyl)-3-aza-bicyclo[3.1.0]hex-6-ylmethyl]-(3-trifluoromethoxy-benzyl)-amide |
| 263 | 531.14 | 532.01 | Thiazole-4-carboxylic acid (3-benzo[1,3]dioxol-5-ylmethyl-3-aza-bicyclo[3.1.0]hex-6-ylmethyl)-(3-trifluoromethoxy-benzyl)-amide |
| 264 | 531.18 | 531.93 | Thiazole-4-carboxylic acid [3-(4-ethoxy-benzyl)-3-aza-bicyclo[3.1.0]hex-6-ylmethyl]-(3-trifluoromethoxy-benzyl)-amide |
| 265 | 529.2 | 530.11 | Thiazole-4-carboxylic acid [3-(4-isopropyl-benzyl)-3-aza-bicyclo[3.1.0]hex-6-ylmethyl]-(3-trifluoromethoxy-benzyl)-amide |
| 266 | 501.17 | 501.91 | Thiazole-4-carboxylic acid [3-(4-methyl-benzyl)-3-aza-bicyclo[3.1.0]hex-6-ylmethyl]-(3-trifluoromethoxy-benzyl)-amide |
| 267 | 537.17 | 538.11 | Thiazole-4-carboxylic acid (3-naphthalen-2-ylmethyl-3-aza-bicyclo[3.1.0]hex-6-ylmethyl)-(3-trifluoromethoxy-benzyl)-amide |
| 268 | 531.14 | 531.92 | Thiazole-4-carboxylic acid (3-benzo[1,3]dioxol-4-ylmethyl-3-aza-bicyclo[3.1.0]hex-6-ylmethyl)-(3-trifluoromethoxy-benzyl)-amide |
| 269 | 523.14 | 524.15 | Thiazole-4-carboxylic acid [3-(2,3-difluoro-benzyl)-3-aza-bicyclo[3.1.0]hex-6-ylmethyl]-(3-trifluoromethoxy-benzyl)-amide |
| 270 | 523.14 | 523.90 | Thiazole-4-carboxylic acid [3-(2,5-difluoro-benzyl)-3-aza-bicyclo[3.1.0]hex-6-ylmethyl]-(3-trifluoromethoxy-benzyl)-amide |
| 271 | 538.17 | 539.06 | Thiazole-4-carboxylic acid (3-quinolin-7-ylmethyl-3-aza-bicyclo[3.1.0]hex-6-ylmethyl)-(3-trifluoromethoxy-benzyl)-amide |
| 272 | 531.18 | 531.94 | Thiazole-4-carboxylic acid [3-(4-methoxy-3-methyl-benzyl)-3-aza-bicyclo[3.1.0]hex-6-ylmethyl]-(3-trifluoromethoxy-benzyl)-amide |
| 273 | 523.14 | 524.02 | Thiazole-4-carboxylic acid [3-(2,4-difluoro-benzyl)-3-aza-bicyclo[3.1.0]hex-6-ylmethyl]-(3-trifluoromethoxy-benzyl)-amide |
| 274 | 533.2 | 533.96 | Thiazole-4-carboxylic acid {3-[3-(5-methyl-furan-2-yl)-butyl]-3-aza-bicyclo[3.1.0]hex-6-ylmethyl}-(3-trifluoromethoxy-benzyl)-amide |
| 275 | 554.17 | 554.90 | Thiazole-4-carboxylic acid [3-(1-pyrimidin-2-yl-1H-pyrrol-2-ylmethyl)-3-aza-bicyclo[3.1.0]hex-6-ylmethyl]-(3-trifluoromethoxy-benzyl)-amide |
| 276 | 523.14 | 524.09 | Thiazole-4-carboxylic acid [3-(3,5-difluoro-benzyl)-3-aza-bicyclo[3.1.0]hex-6-ylmethyl]-(3-trifluoromethoxy-benzyl)-amide |
| 277 | 553.15 | 554.09 | Thiazole-4-carboxylic acid [3-(4-difluoromethoxy-benzyl)-3-aza-bicyclo[3.1.0]hex-6-ylmethyl]-(3-trifluoromethoxy-benzyl)-amide |
| 278 | 538.17 | 539.05 | Thiazole-4-carboxylic acid (3-quinolin-8-ylmethyl-3-aza-bicyclo[3.1.0]hex-6-ylmethyl)-(3-trifluoromethoxy-benzyl)-amide |
| 279 | 533.21 | 534.02 | Thiazole-4-carboxylic acid [3-(2-butyl-1H-imidazol-4-ylmethyl)-3-aza-bicyclo[3.1.0]hex-6-ylmethyl]-(3-trifluoromethoxy-benzyl)-amide |
| 280 | 526.17 | 526.93 | Thiazole-4-carboxylic acid [3-(1H-indol-2-ylmethyl)-3-aza-bicyclo[3.1.0]hex-6-ylmethyl]-(3-trifluoromethoxy-benzyl)-amide |
| 281 | 530.14 | 530.96 | Thiazole-4-carboxylic acid [3-(3-cyano-4-fluoro-benzyl)-3-aza-bicyclo[3.1.0]hex-6-ylmethyl]-(3-trifluoromethoxy-benzyl)-amide |
| 282 | 526.17 | 526.90 | Thiazole-4-carboxylic acid [3-(1H-indol-5-ylmethyl)-3-aza-bicyclo[3.1.0]hex-6-ylmethyl]-(3-trifluoromethoxy-benzyl)-amide |
| 283 | 535.16 | 536.09 | Thiazole-4-carboxylic acid [3-(2-fluoro-4-methoxy-benzyl)-3-aza-bicyclo[3.1.0]hex-6-ylmethyl]-(3-trifluoromethoxy-benzyl)-amide |
| 284 | 527.16 | 527.99 | Thiazole-4-carboxylic acid [3-(1H-benzoimidazol-2-ylmethyl)-3-aza-bicyclo[3.1.0]hex-6-ylmethyl]-(3-trifluoromethoxy-benzyl)-amide |
| 285 | 528.07 | 528.79 | Thiazole-4-carboxylic acid [3-(2-chloro-thiazol-5-ylmethyl)-3-aza-bicyclo[3.1.0]hex-6-ylmethyl]-(3-trifluoromethoxy-benzyl)-amide |
| 286 | 525.12 | 526.02 | Thiazole-4-carboxylic acid [3-(4-chloro-1-methyl-1H-pyrazol-3-ylmethyl)-3-aza-bicyclo[3.1.0]hex-6-ylmethyl]-(3-trifluoromethoxy-benzyl)-amide |
| 287 | 540.23 | 541.2 | 1-Methyl-1H-imidazole-4-carboxylic acid [3-(2-hydroxy-indan-2-ylmethyl)-3-aza-bicyclo[3.1.0]hex-6-ylmethyl]-(3-trifluoromethoxy-benzyl)-amide |
| 288 | 456.23 | 457.2/ 459.2 | 1-Methyl-1H-imidazole-4-carboxylic acid (3-chloro-benzyl)-[3-(1-hydroxy-cyclohexylmethyl)-3-aza-bicyclo[3.1.0]hex-6-ylmethyl]-amide |
| 289 | 490.21 | 491.3/ 493.3 | 1-Methyl-1H-imidazole-4-carboxylic acid (3-chloro-benzyl)-[3-(2-hydroxy-indan-2-ylmethyl)-3-aza-bicyclo[3.1.0]hex-6-ylmethyl]-amide |
| 290 | 490.26 | 491.1 | 1-Methyl-1H-imidazole-4-carboxylic acid [3-(1-hydroxy-cyclohexylmethyl)-3-aza-bicyclo[3.1.0]hex-6-ylmethyl]-(3-trifluoromethyl-benzyl)-amide |
| 291 | 476.24 | 477.2 | 1-Methyl-1H-imidazole-4-carboxylic acid [3-(1-hydroxy-cyclopentylmethyl)-3-aza-bicyclo[3.1.0]hex-6-ylmethyl]-(3-trifluoromethyl-benzyl)-amide |
| 292 | 460.24 | 461.1 | 1-Methyl-1H-imidazole-4-carboxylic acid (3-cyclopentylmethyl-3-aza-bicyclo[3.1.0]hex-6-ylmethyl)-(3-trifluoromethyl-benzyl)-amide |
| 3293 | 370.27 | 371.2 | 1-Methyl-1H-imidazole-4-carboxylic acid cyclohexylmethyl-(3-cyclopropylmethyl-3-aza-bicyclo[3.1.0]hex-6-ylmethyl)-amide |
| 294 | 466.22 | 467.0 | 1-Methyl-1H-imidazole-4-carboxylic acid [3-(2-hydroxy-2-methyl-propyl)-3-aza-bicyclo[3.1.0]hex-6-ylmethyl]-(3-trifluoromethoxy-benzyl)-amide |
| 295 | 490.18 | 491.0 | 1-Methyl-1H-imidazole-4-carboxylic acid (3-trifluoromethoxy-benzyl)-[3-(3,3,3-trifluoro-propyl)-3-aza-bicyclo[3.1.0]hex-6-ylmethyl]-amide |
| 296 | 462.22 | 463.1 | 1-Methyl-1H-imidazole-4-carboxylic acid (3-cyclopentyl-3-aza-bicyclo[3.1.0]hex-6-ylmethyl)-(3-trifluoromethoxy-benzyl)-amide |

| Example | MW Calc | Mass Spec Data (M + 1) | IUPAC Name |
|---|---|---|---|
| 297 | 448.21 | 449.0 | 1-Methyl-1H-imidazole-4-carboxylic acid (3-cyclobutyl-3-aza-bicyclo[3.1.0]hex-6-ylmethyl)-(3-trifluoromethoxy-benzyl)-amide |
| 298 | 440.23 | 442.1 | 1-Methyl-1H-imidazole-4-carboxylic acid [3-(4-chloro-benzyl)-3-aza-bicyclo[3.1.0]hex-6-ylmethyl]-cyclohexylmethyl-amide |
| 299 | 478.22 | 479.0 | 1-Methyl-1H-imidazole-4-carboxylic acid [3-(2-hydroxy-cyclopentyl)-3-aza-bicyclo[3.1.0]hex-6-ylmethyl]-(3-trifluoromethoxy-benzyl)-amide |
| 300 | 436.21 | 437.08 | 1,5-Dimethyl-1H-pyrazole-3-carboxylic acid (3-ethyl-3-aza-bicyclo[3.1.0]hex-6-ylmethyl)-(3-trifluoromethoxy-benzyl)-amide |
| 301 | 423.18 | 424.08 | 5-Methyl-isoxazole-3-carboxylic acid (3-ethyl-3-aza-bicyclo[3.1.0]hex-6-ylmethyl)-(3-trifluoromethoxy-benzyl)-amide |
| 302 | 493.06 | 493.89 | 4,5-Dichloro-isothiazole-3-carboxylic acid (3-ethyl-3-aza-bicyclo[3.1.0]hex-6-ylmethyl)-(3-trifluoromethoxy-benzyl)-amide |
| 303 | 451.21 | 452.07 | 5-Propyl-isoxazole-3-carboxylic acid (3-ethyl-3-aza-bicyclo[3.1.0]hex-6-ylmethyl)-(3-trifluoromethoxy-benzyl)-amide |
| 304 | 389.16 | 390 | Thiazole-4-carboxylic acid (3-aza-bicyclo[3.1.0]hex-6-ylmethyl)-(4-fluoro-3-isopropoxy-benzyl)-amide |
| 305 | 415.17 | 416.0 | Thiazole-4-carboxylic acid (3-aza-bicyclo[3.1.0]hex-6-ylmethyl)-(3-cyclopentyloxy-4-fluoro-benzyl)-amide |
| 306 | 417.19 | 418.0 | Thiazole-4-carboxylic acid (3-aza-bicyclo[3.1.0]hex-6-ylmethyl)-[3-(2,2-dimethyl-propoxy)-4-fluoro-benzyl]-amide |
| 307 | 429.19 | 430.0 | Thiazole-4-carboxylic acid (3-aza-bicyclo[3.1.0]hex-6-ylmethyl)-(3-cyclohexyloxy-4-fluoro-benzyl)-amide |
| 308 | 378.1 | 379 | 1-Methyl-1H-imidazole-4-carboxylic acid (3-aza-bicyclo[3.1.0]hex-6-ylmethyl)-(3,5-dichloro-benzyl)-amide |
| 309 | 436.21 | 437.1 | 1-Methyl-1H-imidazole-4-carboxylic acid (3-isopropyl-3-aza-bicyclo[3.1.0]hex-6-ylmethyl)-(3-trifluoromethoxy-benzyl)-amide |
| 310 | 469.2 | 470.2 | Quinoline-2-carboxylic acid (3-ethyl-3-aza-bicyclo[3.1.0]hex-6-ylmethyl)-(3-trifluoromethoxy-benzyl)-amide |
| 311 | 419.18 | 420.24 | Pyridine-2-carboxylic acid (3-ethyl-3-aza-bicyclo[3.1.0]hex-6-ylmethyl)-(3-trifluoromethoxy-benzyl)-amide |
| 312 | 423.18 | 424.25 | 5-Methyl-isoxazole-3-carboxylic acid (3-ethyl-3-aza-bicyclo[3.1.0]hex-6-ylmethyl)-(3-trifluoromethoxy-benzyl)-amide |
| 313 | 437.19 | 438.20 | 5-Ethyl-isoxazole-3-carboxylic acid (3-ethyl-3-aza-bicyclo[3.1.0]hex-6-ylmethyl)-(3-trifluoromethoxy-benzyl)-amide |
| 314 | 469.2 | 470.23 | Quinoline-4-carboxylic acid (3-ethyl-3-aza-bicyclo[3.1.0]hex-6-ylmethyl)-(3-trifluoromethoxy-benzyl)-amide |
| 315 | 448.21 | 449.21 | 5-Cyclopropyl-2H-pyrazole-3-carboxylic acid (3-ethyl-3-aza-bicyclo[3.1.0]hex-6-ylmethyl)-(3-trifluoromethoxy-benzyl)-amide |
| 316 | 436.21 | 437.26 | 1,5-Dimethyl-1H-pyrazole-3-carboxylic acid (3-ethyl-3-aza-bicyclo[3.1.0]hex-6-ylmethyl)-(3-trifluoromethoxy-benzyl)-amide |
| 317 | 450.22 | 451.26 | 2-Ethyl-5-methyl-2H-pyrazole-3-carboxylic acid (3-ethyl-3-aza-bicyclo[3.1.0]hex-6-ylmethyl)-(3-trifluoromethoxy-benzyl)-amide |
| 318 | 422.19 | 423.21 | 4-Methyl-1H-imidazole-2-carboxylic acid (3-ethyl-3-aza-bicyclo[3.1.0]hex-6-ylmethyl)-(3-trifluoromethoxy-benzyl)-amide |
| 319 | 451.21 | 452.23 | 5-Propyl-isoxazole-3-carboxylic acid (3-ethyl-3-aza-bicyclo[3.1.0]hex-6-ylmethyl)-(3-trifluoromethoxy-benzyl)-amide |
| 320 | 450.22 | 451.24 | 5-Isopropyl-2H-pyrazole-3-carboxylic acid (3-ethyl-3-aza-bicyclo[3.1.0]hex-6-ylmethyl)-(3-trifluoromethoxy-benzyl)-amide |
| 321 | 422.19 | 423.21 | 1-Methyl-1H-pyrazole-3-carboxylic acid (3-ethyl-3-aza-bicyclo[3.1.0]hex-6-ylmethyl)-(3-trifluoromethoxy-benzyl)-amide |
| 322 | 450.22 | 451.24 | 5-Ethyl-2-methyl-2H-pyrazole-3-carboxylic acid (3-ethyl-3-aza-bicyclo[3.1.0]hex-6-ylmethyl)-(3-trifluoromethoxy-benzyl)-amide |
| 323 | 467.19 | 468.21 | 2-Isopropyl-thiazole-4-carboxylic acid (3-ethyl-3-aza-bicyclo[3.1.0]hex-6-ylmethyl)-(3-trifluoromethoxy-benzyl)-amide |
| 324 | 422.19 | 423.21 | 1-Methyl-1H-imidazole-4-carboxylic acid (3-ethyl-3-aza-bicyclo[3.1.0]hex-6-ylmethyl)-(3-trifluoromethoxy-benzyl)-amide |
| 325 | 425.14 | 426.18 | Thiazole-4-carboxylic acid (3-ethyl-3-aza-bicyclo[3.1.0]hex-6-ylmethyl)-(3-trifluoromethoxy-benzyl)-amide |
| 326 | 453.14 | 454.16 | 5-Chloro-pyridine-2-carboxylic acid (3-ethyl-3-aza-bicyclo[3.1.0]hex-6-ylmethyl)-(3-trifluoromethoxy-benzyl)-amide |
| 327 | 386.23 | 386.81 | 1-Methyl-1H-imidazole-4-carboxylic acid pentyl-[3-(3,3,3-trifluoro-propyl)-3-aza-bicyclo[3.1.0]hex-6-ylmethyl]-amide |
| 328 | 386.23 | 386.94 | 1-Methyl-1H-imidazole-4-carboxylic acid (2-methyl-butyl)-[3-(3,3,3-trifluoro-propyl)-3-aza-bicyclo[3.1.0]hex-6-ylmethyl]-amide |
| 329 | 400.24 | 401.20 | 1-Methyl-1H-imidazole-4-carboxylic acid (2-ethyl-butyl)-[3-(3,3,3-trifluoro-propyl)-3-aza-bicyclo[3.1.0]hex-6-ylmethyl]-amide |
| 330 | 370.2 | 371.13 | 1-Methyl-1H-imidazole-4-carboxylic acid cyclopropylmethyl-[3-(3,3,3-trifluoro-propyl)-3-aza-bicyclo[3.1.0]hex-6-ylmethyl]-amide |
| 331 | 414.26 | 415.29 | 1-Methyl-1H-imidazole-4-carboxylic acid heptyl-[3-(3,3,3-trifluoro-propyl)-3-aza-bicyclo[3.1.0]hex-6-ylmethyl]-amide |
| 332 | 372.21 | 373.22 | 1-Methyl-1H-imidazole-4-carboxylic acid butyl-[3-(3,3,3-trifluoro-propyl)-3-aza-bicyclo[3.1.0]hex-6-ylmethyl]-amide |
| 333 | 412.24 | 413.22 | 1-Methyl-1H-imidazole-4-carboxylic acid cyclohexylmethyl-[3-(3,3,3-trifluoro-propyl)-3-aza-bicyclo[3.1.0]hex-6-ylmethyl]-amide |
| 334 | 414.22 | 415.20 | 1-Methyl-1H-imidazole-4-carboxylic acid [3-(4-chloro-benzyl)-3-aza-bicyclo[3.1.0]hex-6-ylmethyl]-(2-methyl-butyl)-amide |
| 335 | 426.26 | 427.21 | 1-Methyl-1H-imidazole-4-carboxylic acid (3-cyclopentyl-propyl)-[3-(3,3,3-trifluoro-propyl)-3-aza-bicyclo[3.1.0]hex-6-ylmethyl]-amide |
| 336 | 414.22 | 415.19 | 1-Methyl-1H-imidazole-4-carboxylic acid [3-(4-chloro-benzyl)-3-aza-bicyclo[3.1.0]hex-6-ylmethyl]-pentyl-amide |
| 337 | 400.2 | 401.21 | 1-Methyl-1H-imidazole-4-carboxylic acid butyl-[3-(4-chloro-benzyl)-3-aza-bicyclo[3.1.0]hex-6-ylmethyl]-amide |
| 338 | 398.19 | 399.14 | 1-Methyl-1H-imidazole-4-carboxylic acid [3-(4-chloro-benzyl)-3-aza-bicyclo[3.1.0]hex-6-ylmethyl]-cyclopropylmethyl-amide |
| 339 | 428.23 | 429.28 | 1-Methyl-1H-imidazole-4-carboxylic acid [3-(4-chloro-benzyl)-3-aza-bicyclo[3.1.0]hex-6-ylmethyl]-(2-ethyl-butyl)-amide |
| 340 | 440.16 | 441.1 | 1-Methyl-1H-imidazole-4-carboxylic acid (3-chloro-benzyl)-[3-(3,3,3-trifluoro-propyl)-3-aza-bicyclo[3.1.0]hex-6-ylmethyl]-amide |
| 341 | 428.2 | 429.1 | 1-Methyl-1H-imidazole-4-carboxylic acid (3-chloro-benzyl)-[3-(tetrahydro-pyran-4- |

-continued

| Example | MW Calc | Mass Spec Data (M + 1) | IUPAC Name |
|---|---|---|---|
| 342 | 492.18 | 493.1 | 1-Methyl-1H-imidazole-4-carboxylic acid (4-fluoro-3-trifluoromethyl-benzyl)-[3-(3,3,3-trifluoro-propyl)-3-aza-bicyclo[3.1.0]hex-6-ylmethyl]-amide |
| 343 | 508.23 | 509.2 | 1-Methyl-1H-imidazole-4-carboxylic acid [3-(4-hydroxy-tetrahydro-pyran-4-ylmethyl)-3-aza-bicyclo[3.1.0]hex-6-ylmethyl]-(3-trifluoromethoxy-benzyl)-amide |
| 344 | 458.21 | 459.2 | 1-Methyl-1H-imidazole-4-carboxylic acid (3-chloro-benzyl)-[3-(4-hydroxy-tetrahydro-pyran-4-ylmethyl)-3-aza-bicyclo[3.1.0]hex-6-ylmethyl]-amide |
| 345 | 478.22 | 479.2 | 1-Methyl-1H-imidazole-4-carboxylic acid [3-(tetrahydro-pyran-4-yl)-3-aza-bicyclo[3.1.0]hex-6-ylmethyl]-(3-trifluoromethoxy-benzyl)-amide |
| 346 | 480.21 | 481.2 | 1-Methyl-1H-imidazole-4-carboxylic acid (4-fluoro-3-trifluoromethyl-benzyl)-[3-(tetrahydro-pyran-4-yl)-3-aza-bicyclo[3.1.0]hex-6-ylmethyl]-amide |
| 347 | 330.24 | 331.2 | 1-Methyl-1H-imidazole-4-carboxylic acid cyclohexylmethyl-(3-methyl-3-aza-bicyclo[3.1.0]hex-6-ylmethyl)-amide |
| 348 | 344.26 | 345.3 | 1-Methyl-1H-imidazole-4-carboxylic acid cyclohexylmethyl-(3-ethyl-3-aza-bicyclo[3.1.0]hex-6-ylmethyl)-amide |
| 349 | 426.14 | 427.1 | 2-Chloro-N-(3-methyl-3-aza-bicyclo[3.1.0]hex-6-ylmethyl)-N-(1-methyl-1H-imidazol-4-ylmethyl)-3-trifluoromethyl-benzamide |
| 350 | 434.19 | 435.1 | 6,7-Dihydro-5H-pyrrolo[1,2-a]imidazole-2-carboxylic acid (3-methyl-3-aza-bicyclo[3.1.0]hex-6-ylmethyl)-(3-trifluoromethoxy-benzyl)-amide |
| 351 | 372.17 | 373.2 | 3-Chloro-N-(3-ethyl-3-aza-bicyclo[3.1.0]hex-6-ylmethyl)-N-(1-methyl-1H-imidazol-4-ylmethyl)-benzamide |
| 352 | 468.19 | 469.28 | 1-Propyl-1H-imidazole-4-carboxylic acid (3-chloro-benzyl)-[3-(3,3,3-trifluoro-propyl)-3-aza-bicyclo[3.1.0]hex-6-ylmethyl]-amide |
| 353 | 586.16 | 587.21 | 1-(4-Trifluoromethoxy-phenyl)-1H-imidazole-4-carboxylic acid (3-chloro-benzyl)-[3-(3,3,3-trifluoro-propyl)-3-aza-bicyclo[3.1.0]hex-6-ylmethyl]-amide |
| 354 | 468.19 | 469.27 | 1-Isopropyl-1H-imidazole-4-carboxylic acid (3-chloro-benzyl)-[3-(3,3,3-trifluoro-propyl)-3-aza-bicyclo[3.1.0]hex-6-ylmethyl]-amide |
| 355 | 560.22 | 561.33 | 1-[2-(4-Trifluoromethoxy-phenyl)-ethyl]-1H-imidazole-4-carboxylic acid (3-chloro-benzyl)-(3-propyl-3-aza-bicyclo[3.1.0]hex-6-ylmethyl)-amide |
| 356 | 414.22 | 415.3 | 1-Propyl-1H-imidazole-4-carboxylic acid (3-chloro-benzyl)-(3-propyl-3-aza-bicyclo[3.1.0]hex-6-ylmethyl)-amide |
| 357 | 516.19 | 517.31 | 1-(4-Trifluoromethyl-phenyl)-1H-imidazole-4-carboxylic acid (3-chloro-benzyl)-(3-propyl-3-aza-bicyclo[3.1.0]hex-6-ylmethyl)-amide |
| 358 | 428.23 | 429.35 | 1-Butyl-1H-imidazole-4-carboxylic acid (3-chloro-benzyl)-(3-propyl-3-aza-bicyclo[3.1.0]hex-6-ylmethyl)-amide |
| 359 | 546.2 | 547.33 | 1-(4-Trifluoromethoxy-benzyl)-1H-imidazole-4-carboxylic acid (3-chloro-benzyl)-(3-propyl-3-aza-bicyclo[3.1.0]hex-6-ylmethyl)-amide |
| 360 | 532.19 | 533.34 | 1-(4-Trifluoromethoxy-phenyl)-1H-imidazole-4-carboxylic acid (3-chloro-benzyl)-(3-propyl-3-aza-bicyclo[3.1.0]hex-6-ylmethyl)-amide |
| 361 | 414.22 | 415.33 | 1-Isopropyl-1H-imidazole-4-carboxylic acid (3-chloro-benzyl)-(3-propyl-3-aza-bicyclo[3.1.0]hex-6-ylmethyl)-amide |
| 362 | 414.22 | 415.33 | 1-Butyl-1H-imidazole-4-carboxylic acid (3-chloro-benzyl)-(3-ethyl-3-aza-bicyclo[3.1.0]hex-6-ylmethyl)-amide |
| 363 | 468.15 | 469.27 | 1-(3-Chloro-phenyl)-1H-imidazole-4-carboxylic acid (3-chloro-benzyl)-(3-ethyl-3-aza-bicyclo[3.1.0]hex-6-ylmethyl)-amide |
| 364 | 400.2 | 401.31 | 1-Propyl-1H-imidazole-4-carboxylic acid (3-chloro-benzyl)-(3-ethyl-3-aza-bicyclo[3.1.0]hex-6-ylmethyl)-amide |
| 365 | 400.2 | 401.31 | 1-Isopropyl-1H-imidazole-4-carboxylic acid (3-chloro-benzyl)-(3-ethyl-3-aza-bicyclo[3.1.0]hex-6-ylmethyl)-amide |
| 366 | 518.17 | 519.29 | 1-(4-Trifluoromethoxy-phenyl)-1H-imidazole-4-carboxylic acid (3-chloro-benzyl)-(3-ethyl-3-aza-bicyclo[3.1.0]hex-6-ylmethyl)-amide |
| 367 | 472.18 | 473.1 | 1-Methyl-1H-imidazole-4-carboxylic acid (3-pyrazin-2-yl-3-aza-bicyclo[3.1.0]hex-6-ylmethyl)-(3-trifluoromethoxy-benzyl)-amide |
| 368 | 510.2 | 511.2 | 1-Methyl-1H-imidazole-4-carboxylic acid [3-(1H-benzoimidazol-2-yl)-3-aza-bicyclo[3.1.0]hex-6-ylmethyl]-(3-trifluoromethoxy-benzyl)-amide |
| 369 | 463.22 | 464.2 | 1-Methyl-1H-imidazole-4-carboxylic acid [3-(1-methyl-azetidin-3-yl)-3-aza-bicyclo[3.1.0]hex-6-ylmethyl]-(3-trifluoromethoxy-benzyl)-amide |
| 370 | 399.18 | 400.2 | 1-Methyl-1H-imidazole-4-carboxylic acid (3-azetidin-3-yl-3-aza-bicyclo[3.1.0]hex-6-ylmethyl)-(3-chloro-benzyl)-amide |
| 371 | 362.83 | 363.1 | N-(3-chloro-4-fluorobenzyl)-N-((3-methyl-3-aza-bicyclo[3.1.0]hexan-6-yl)methyl)-1H-imidazole-4-carboxamide |

Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in CDCl$_3$ by a Varian NMR spectrometer (Unity, 400 MHz for $^1$H, 100 MHz for $^{13}$C) unless otherwise indicated and peak positions are expressed in parts per million (ppm) downfield from tetramethylsilane (δ). The peak shapes are denoted as follows: s, singlet; d, doublet; t, triplet; m, multiplet; br, broad.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A pharmaceutical composition comprising the compound of 1-methyl-1H-imidazole-4-carboxylic acid (3-chloro-4-fluoro-benzyl)-(3-methyl-3-aza-bicyclo[3.1.0] hex-6-ylmethyl)-amide, or a pharmaceutically acceptable salt thereof.

2. A method of treating schizophrenia, comprising administering to a mammal in need of such treatment an amount of the compound of 1-methyl-1H-imidazole-4-carboxylic acid (3-chloro-4-fluoro-benzyl)-(3-methyl-3-aza-bicyclo[3.1.0]hex-6-ylmethyl)-amide, or a pharmaceutically acceptable salt thereof, that is effective in treating schizophrenia.

3. The compound of 1-methyl-1H-imidazole-4-carboxylic acid (3-chloro-4-fluoro-benzyl)-(3-methyl-3-aza-bicyclo[3.1.0]hex-6-ylmethyl)-amide, or a pharmaceutically acceptable salt thereof.

* * * * *